(12) United States Patent
Kornegay et al.

(10) Patent No.: US 8,198,422 B2
(45) Date of Patent: Jun. 12, 2012

(54) HIGH-RISK HUMAN PAPILLOMAVIRUS DETECTION

(75) Inventors: Janet Kornegay, Alameda, CA (US);
Carrie L. Aldrich, Tucson, AZ (US);
Stephen G. Will, Cham (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

(21) Appl. No.: 13/237,708

(22) Filed: Sep. 20, 2011

(65) Prior Publication Data

US 2012/0009563 A1    Jan. 12, 2012

Related U.S. Application Data

(62) Division of application No. 12/332,164, filed on Dec. 10, 2008, now Pat. No. 8,058,423, which is a division of application No. 11/119,343, filed on Apr. 29, 2005, now Pat. No. 7,482,142.

(60) Provisional application No. 60/568,934, filed on May 7, 2004.

(51) Int. Cl.
*C07H 23/00*    (2006.01)
*C12Q 1/70*    (2006.01)

(52) U.S. Cl. .................. 536/23.1; 435/5; 424/204.1

(58) Field of Classification Search .............. None
See application file for complete search history.

(56) References Cited

U.S. PATENT DOCUMENTS

| | | | |
|---|---|---|---|
| 5,484,908 | A | 1/1996 | Froehler et al. |
| 5,645,985 | A | 7/1997 | Froehler et al. |
| 5,705,627 | A | 1/1998 | Manos et al. |
| 5,830,653 | A | 11/1998 | Froehler et al. |
| 6,265,154 | B1 | 7/2001 | Kroeger et al. |
| 6,355,424 | B1 | 3/2002 | Lorinez et al. |
| 6,482,588 | B1 | 11/2002 | Van Doorn et al. |
| 7,135,284 | B1 * | 11/2006 | Behlke et al. .......... 435/6.1 |
| 7,741,042 | B2 * | 6/2010 | An et al. ................ 435/6.11 |
| 2003/0059806 | A1 | 3/2003 | Wheeler et al. |

FOREIGN PATENT DOCUMENTS

| | | |
|---|---|---|
| EP | 1 302 550 | 4/2003 |
| WO | 00/63366 | 10/2000 |

OTHER PUBLICATIONS van den Brule et al. General Primer Polymerase Chain Reaction in Combination with Sequence Analysis of Potentially Novel Papillomavirus Genotypes in Cervical Lesions. Journal of Clinical Microbiology, Jul. 1992, vol. 30, No. 7, pp. 1716-1721.
Darby et al. High throughput measurement of duplex, triplex and quadruplex melting curves using molecular beacons and a LightCycler. Nucleic Acids Research, 2002, vol. 30, No. 9, e39, pp. 1-8.
Cole et al. (1986) "Genome organization and nucleotide sequence of human papillomavirus type 33, which is associated with cervical cancer." Journal of Virology, 58: 991-995.
Delius et al. (1994) "Primer-directed sequencing of human papillomavirus types." Current Topics in Microbiology and Immunology, 186: 13-31.
Hubert et al. (1999) "DNA replication of human papillomavirus type 31 is modulated by elements of the upstream regulatory region that lie 5'of the minimal origin." Journal of Virology, 73(3): 1835-1845.
Kirii et al. (1991) "Human papillomavirus type 58 DNA sequence." Virology 185: 424-427.
Manos et al. (1989) "The use of polymerase chain reaction amplification for the detection of genital human papillomaviruses." Cancer Cells 7: 209-214.
Munzo et al. (2003) "Epidemiologic Classification of Human Papillomavirus Types Associated with Cervical Cancer." The New England Journal of Medicine 348(6): 518-627.
Shimoda et al. (1988) "Human papillomavirus type 52: a new virus associated with cervical neoplasia." Journal of General Virology, 69(11): 2925-2928.
Van Den Brule et al. (1990) "General primer-mediated polymerase chain reaction permits the detection of sequenced and still unsequenced human papillomavirus genotypes in cervical scrapes and carcinomas." International Journal of Cancer, 45: 644-649.
Zur Hausen (2002) "Papillomavirus and cancer: from basic studies to clinical application." Nature Reviews, Cancer 2 (5): 342-350.
Van der Brule et al., Journal of Microbiology, 1992, vol. 30, p. 1716-1721.

* cited by examiner

*Primary Examiner* — Agnieszka Boesen
(74) *Attorney, Agent, or Firm* — M. Reza Savari

(57) ABSTRACT

This invention provides compositions and methods for detecting HPV in a sample. This invention also provides related kits, systems, and computers.

6 Claims, 5 Drawing Sheets

SEQUENCE LISTING

<160> NUMBER OF SEQ ID NOS: 31

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cagtactaaa agtcatgtta gtgct                                           25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cagtacaaat agtcatgtta gtgct                                           25

<210> SEQ ID NO 3
<211> LENGTH: 23
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 3
tcatttttat atgtgctttc ctt                                              23

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
attatcattt ttatatgtac tttcctt                                          27

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tcatttttat atgtgccttc ctt                                              23

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ttaaaatttt cattttata tgtactttcc tt                                     32

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cagtacataa agtcatgtta gtgct                                            25

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ttaaaatttt cattttata tgt                                               23

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 9
cataaagtca tgttagtgct gcgagt    26

<210> SEQ ID NO 10
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
atttttatat gtgctttcct tttaattgca gcacaaacag aca    43

<210> SEQ ID NO 11
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
aattgcagca caaacagaca atttttatat gtgctttcct ttt    43

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ttaaaatttt cattttata tgtactttc    29

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13 aaatttcat ttttatatgt actttc    26

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ttaaaattgt cattttata tgtactttc    29

<210> SEQ ID NO 15
<211> LENGTH: 29
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:

```
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: 5-propynyl-d-Uracil
<220> FEATURE:
<221> NAME/KEY: modified_base
<222> LOCATION: (10)..(10)
<223> OTHER INFORMATION: 5-propynyl-d-Uracil
<220> FEATURE:
<221> NAME/KEY: modified_base
<222> LOCATION: (23)..(23)
<223> OTHER INFORMATION: 5-propynyl-d-Uracil
<220> FEATURE:
<221> NAME/KEY: modified_base
<222> LOCATION: (25)..(25)
<223> OTHER INFORMATION: 5-methyl-d-Cytosine
<220> FEATURE:
<221> NAME/KEY: modified_base
<222> LOCATION: (28)..(28)
<223> OTHER INFORMATION: 5-propynyl-d-Uracil

<400> SEQUENCE: 15
ttaaaatutu cattttata tguacttuc                                              29

<210> SEQ ID NO 16
<211> LENGTH: 29
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: 2'-O-methyl Ribo-Uracil
<220> FEATURE:
<221> NAME/KEY: modified_base
<222> LOCATION: (10)..(10)
<223> OTHER INFORMATION: 2'-O-methyl Ribo-Uracil
<220> FEATURE:
<221> NAME/KEY: modified_base
<222> LOCATION: (23)..(23)
<223> OTHER INFORMATION: 2'-O-methyl Ribo-Uracil
<220> FEATURE:
<221> NAME/KEY: modified_base
<222> LOCATION: (25)..(25)
<223> OTHER INFORMATION: 2'-O-methyl Ribo-Cytosine
<220> FEATURE:
<221> NAME/KEY: modified_base
<222> LOCATION: (28)..(28)
<223> OTHER INFORMATION: 2'-O-methyl Ribo-Uracil

<400> SEQUENCE: 16
ttaaaatutu cattttata tguacttuc                                              29

<210> SEQ ID NO 17
<211> LENGTH: 29
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 5-propynyl-d-Uracil
<220> FEATURE:
<221> NAME/KEY: modified_base
```

```
<222> LOCATION: (10)..(10)
<223> OTHER INFORMATION: 5-propynyl-d-Uracil
<220> FEATURE:
<221> NAME/KEY: modified_base
<222> LOCATION: (11)..(11)
<223> OTHER INFORMATION: 5-methyl-d-Cytosine
<220> FEATURE:
<221> NAME/KEY: modified_base
<222> LOCATION: (13)..(17)
<223> OTHER INFORMATION: 5-propynyl-d-Uracil
<220> FEATURE:
<221> NAME/KEY: modified_base
<222> LOCATION: (19)..(19)
<223> OTHER INFORMATION: 5-propynyl-d-Uracil
<220> FEATURE:
<221> NAME/KEY: modified_base
<222> LOCATION: (21)..(21)
<223> OTHER INFORMATION: 5-propynyl-d-Uracil
<220> FEATURE:
<221> NAME/KEY: modified_base
<222> LOCATION: (23)..(23)
<223> OTHER INFORMATION: 5-propynyl-d-Uracil
<220> FEATURE:
<221> NAME/KEY: modified_base
<222> LOCATION: (25)..(25)
<223> OTHER INFORMATION: 5-methyl-d-Cytosine
<220> FEATURE:
<221> NAME/KEY: modified_base
<222> LOCATION: (28)..(28)
<223> OTHER INFORMATION: 5-propynyl-d-Uracil

<400> SEQUENCE: 17
ttaaaauutu cauuuuuaua uguacttuc                                       29

<210> SEQ ID NO 18
<211> LENGTH: 32
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 18
cataaagtca tattagtgct gcgagtggta tc                                   32

<210> SEQ ID NO 19
<211> LENGTH: 32
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: 5-propynyl-d-Uracil
<220> FEATURE:
<221> NAME/KEY: modified_base
<222> LOCATION: (19)..(19)
<223> OTHER INFORMATION: 5-methyl-d-Cytosine
<220> FEATURE:
<221> NAME/KEY: modified_base
<222> LOCATION: (22)..(22)
<223> OTHER INFORMATION: 5-methyl-d-Cytosine

<400> SEQUENCE: 19
cataaagtca uattagtgct gcgagtggta tc                                   32
```

```
<210> SEQ ID NO 20
<211> LENGTH: 29
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: 5-propynyl-d-Uracil
<220> FEATURE:
<221> NAME/KEY: modified_base
<222> LOCATION: (10)..(10)
<223> OTHER INFORMATION: 5-propynyl-d-Uracil
<220> FEATURE:
<221> NAME/KEY: modified_base
<222> LOCATION: (23)..(23)
<223> OTHER INFORMATION: 5-propynyl-d-Uracil
<220> FEATURE:
<221> NAME/KEY: modified_base
<222> LOCATION: (25)..(25)
<223> OTHER INFORMATION: 5-methyl-d-Cytosine
<220> FEATURE:
<221> NAME/KEY: modified_base
<222> LOCATION: (28)..(28)
<223> OTHER INFORMATION: 5-propynyl-d-Uracil

<400> SEQUENCE: 20
ttaaaatugu catttttata tguacttuc                                    29

<210> SEQ ID NO 21
<211> LENGTH: 29
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 5-propynyl-d-Uracil
<220> FEATURE:
<221> NAME/KEY: modified_base
<222> LOCATION: (10)..(10)
<223> OTHER INFORMATION: 5-propynyl-d-Uracil
<220> FEATURE:
<221> NAME/KEY: modified_base
<222> LOCATION: (11)..(11)
<223> OTHER INFORMATION: 5-methyl-d-Cytosine
<220> FEATURE:
<221> NAME/KEY: modified_base
<222> LOCATION: (13)..(17)
<223> OTHER INFORMATION: 5-propynyl-d-Uracil
<220> FEATURE:
<221> NAME/KEY: modified_base
<222> LOCATION: (19)..(19)
<223> OTHER INFORMATION: 5-propynyl-d-Uracil
<220> FEATURE:
<221> NAME/KEY: modified_base
<222> LOCATION: (21)..(21)
<223> OTHER INFORMATION: 5-propynyl-d-Uracil
<220> FEATURE:
<221> NAME/KEY: modified_base
<222> LOCATION: (23)..(23)
<223> OTHER INFORMATION: 5-propynyl-d-Uracil
<220> FEATURE:
<221> NAME/KEY: modified_base
<222> LOCATION: (25)..(25)
<223> OTHER INFORMATION: 5-methyl-d-Cytosine
<220> FEATURE:
<221> NAME/KEY: modified_base
```

```
<222> LOCATION: (28)..(28)
<223> OTHER INFORMATION: 5-propynyl-d-Uracil

<400> SEQUENCE: 21
ttaaaauugu cauuuuaua uguacttuc                                              29

<210> SEQ ID NO 22
<211> LENGTH: 35
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: 5-methyl-d-Cytosine
<220> FEATURE:
<221> NAME/KEY: modified_base
<222> LOCATION: (7)..(8)
<223> OTHER INFORMATION: 5-propynyl-d-Uracil
<220> FEATURE:
<221> NAME/KEY: modified_base
<222> LOCATION: (13)..(14)
<223> OTHER INFORMATION: 5-propynyl-d-Uracil
<220> FEATURE:
<221> NAME/KEY: modified_base
<222> LOCATION: (16)..(16)
<223> OTHER INFORMATION: 5-propynyl-d-Uracil
<220> FEATURE:
<221> NAME/KEY: modified_base
<222> LOCATION: (17)..(17)
<223> OTHER INFORMATION: 5-methyl-d-Cytosine
<220> FEATURE:
<221> NAME/KEY: modified_base
<222> LOCATION: (19)..(19)
<223> OTHER INFORMATION: 5-propynyl-d-Uracil
<220> FEATURE:
<221> NAME/KEY: modified_base
<222> LOCATION: (25)..(25)
<223> OTHER INFORMATION: 5-propynyl-d-Uracil
<220> FEATURE:
<221> NAME/KEY: modified_base
<222> LOCATION: (27)..(27)
<223> OTHER INFORMATION: 5-propynyl-d-Uracil
<220> FEATURE:
<221> NAME/KEY: modified_base
<222> LOCATION: (29)..(29)
<223> OTHER INFORMATION: 5-propynyl-d-Uracil
<220> FEATURE:
<221> NAME/KEY: modified_base
<222> LOCATION: (31)..(31)
<223> OTHER INFORMATION: 5-methyl-d-Cytosine
<220> FEATURE:
<221> NAME/KEY: modified_base
<222> LOCATION: (32)..(34)
<223> OTHER INFORMATION: 5-propynyl-d-Uracil
<220> FEATURE:
<221> NAME/KEY: modified_base
<222> LOCATION: (35)..(35)
<223> OTHER INFORMATION: 5-methyl-d-Cytosine

<400> SEQUENCE: 22
tattccuuaa aauugucaut tttauaugua cuuuc                                      35

<210> SEQ ID NO 23
<211> LENGTH: 30
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
```

-continued

```
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 5-methyl-d-Cytosine
<220> FEATURE:
<221> NAME/KEY: modified_base
<222> LOCATION: (2)..(3)
<223> OTHER INFORMATION: 5-propynyl-d-Uracil
<220> FEATURE:
<221> NAME/KEY: modified_base
<222> LOCATION: (8)..(9)
<223> OTHER INFORMATION: 5-propynyl-d-Uracil
<220> FEATURE:
<221> NAME/KEY: modified_base
<222> LOCATION: (11)..(11)
<223> OTHER INFORMATION: 5-propynyl-d-Uracil
<220> FEATURE:
<221> NAME/KEY: modified_base
<222> LOCATION: (12)..(12)
<223> OTHER INFORMATION: 5-methyl-d-Cytosine
<220> FEATURE:
<221> NAME/KEY: modified_base
<222> LOCATION: (14)..(14)
<223> OTHER INFORMATION: 5-propynyl-d-Uracil
<220> FEATURE:
<221> NAME/KEY: modified_base
<222> LOCATION: (20)..(20)
<223> OTHER INFORMATION: 5-propynyl-d-Uracil
<220> FEATURE:
<221> NAME/KEY: modified_base
<222> LOCATION: (22)..(22)
<223> OTHER INFORMATION: 5-propynyl-d-Uracil
<220> FEATURE:
<221> NAME/KEY: modified_base
<222> LOCATION: (24)..(24)
<223> OTHER INFORMATION: 5-propynyl-d-Uracil
<220> FEATURE:
<221> NAME/KEY: modified_base
<222> LOCATION: (26)..(26)
<223> OTHER INFORMATION: 5-methyl-d-Cytosine
<220> FEATURE:
<221> NAME/KEY: modified_base
<222> LOCATION: (27)..(29)
<223> OTHER INFORMATION: 5-propynyl-d-Uracil
<220> FEATURE:
<221> NAME/KEY: modified_base
<222> LOCATION: (30)..(30)
<223> OTHER INFORMATION: 5-methyl-d-Cytosine

<400> SEQUENCE: 23
cuuaaaauug ucauttttau auguacuuuc                                      30

<210> SEQ ID NO 24
<211> LENGTH: 31
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: 5-propynyl-d-Uracil
<220> FEATURE:
<221> NAME/KEY: modified_base
<222> LOCATION: (12)..(12)
<223> OTHER INFORMATION: 5-propynyl-d-Uracil
<220> FEATURE:
<221> NAME/KEY: modified_base
<222> LOCATION: (25)..(25)
<223> OTHER INFORMATION: 5-propynyl-d-Uracil
<220> FEATURE:
<221> NAME/KEY: modified_base
```

```
<222> LOCATION: (27)..(27)
<223> OTHER INFORMATION: 5-methyl-d-Cytosine
<220> FEATURE:
<221> NAME/KEY: modified_base
<222> LOCATION: (30)..(30)
<223> OTHER INFORMATION: 5-propynyl-d-Uracil

<400> SEQUENCE: 24
ccttaaaatu tcatttttta tatguacttu c                                             31

<210> SEQ ID NO 25
<211> LENGTH: 31
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 5-methyl-d-Cytosine
<220> FEATURE:
<221> NAME/KEY: modified_base
<222> LOCATION: (3)..(4)
<223> OTHER INFORMATION: 5-propynyl-d-Uracil
<220> FEATURE:
<221> NAME/KEY: modified_base
<222> LOCATION: (9)..(10)
<223> OTHER INFORMATION: 5-propynyl-d-Uracil
<220> FEATURE:
<221> NAME/KEY: modified_base
<222> LOCATION: (12)..(12)
<223> OTHER INFORMATION: 5-propynyl-d-Uracil
<220> FEATURE:
<221> NAME/KEY: modified_base
<222> LOCATION: (13)..(13)
<223> OTHER INFORMATION: 5-methyl-d-Cytosine
<220> FEATURE:
<221> NAME/KEY: modified_base
<222> LOCATION: (15)..(15)
<223> OTHER INFORMATION: 5-propynyl-d-Uracil
<220> FEATURE:
<221> NAME/KEY: modified_base
<222> LOCATION: (23)..(23)
<223> OTHER INFORMATION: 5-propynyl-d-Uracil
<220> FEATURE:
<221> NAME/KEY: modified_base
<222> LOCATION: (25)..(25)
<223> OTHER INFORMATION: 5-propynyl-d-Uracil
<220> FEATURE:
<221> NAME/KEY: modified_base
<222> LOCATION: (27)..(27)
<223> OTHER INFORMATION: 5-methyl-d-Cytosine
<220> FEATURE:
<221> NAME/KEY: modified_base
<222> LOCATION: (30)..(30)
<223> OTHER INFORMATION: 5-propynyl-d-Uracil
<220> FEATURE:
<221> NAME/KEY: modified_base
<222> LOCATION: (31)..(31)
<223> OTHER INFORMATION: 5-methyl-d-Cytosine

<400> SEQUENCE: 25
ccuuaaaauu tcautttta tauguacttu c                                              31

<210> SEQ ID NO 26
<211> LENGTH: 31
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
```

<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: 5-propynyl-d-Uracil
<220> FEATURE:
<221> NAME/KEY: modified_base
<222> LOCATION: (12)..(12)
<223> OTHER INFORMATION: 5-propynyl-d-Uracil
<220> FEATURE:
<221> NAME/KEY: modified_base
<222> LOCATION: (25)..(25)
<223> OTHER INFORMATION: 5-propynyl-d-Uracil
<220> FEATURE:
<221> NAME/KEY: modified_base
<222> LOCATION: (27)..(27)
<223> OTHER INFORMATION: 5-methyl-d-Cytosine
<220> FEATURE:
<221> NAME/KEY: modified_base
<222> LOCATION: (30)..(30)
<223> OTHER INFORMATION: 5-propynyl-d-Uracil

<400> SEQUENCE: 26
ccttaaaatu gucattttta tatgugctgu c                                  31

<210> SEQ ID NO 27
<211> LENGTH: 31
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 5-methyl-d-Cytosine
<220> FEATURE:
<221> NAME/KEY: modified_base
<222> LOCATION: (3)..(4)
<223> OTHER INFORMATION: 5-propynyl-d-Uracil
<220> FEATURE:
<221> NAME/KEY: modified_base
<222> LOCATION: (9)..(10)
<223> OTHER INFORMATION: 5-propynyl-d-Uracil
<220> FEATURE:
<221> NAME/KEY: modified_base
<222> LOCATION: (12)..(12)
<223> OTHER INFORMATION: 5-propynyl-d-Uracil
<220> FEATURE:
<221> NAME/KEY: modified_base
<222> LOCATION: (13)..(13)
<223> OTHER INFORMATION: 5-methyl-d-Cytosine
<220> FEATURE:
<221> NAME/KEY: modified_base
<222> LOCATION: (15)..(15)
<223> OTHER INFORMATION: 5-propynyl-d-Uracil
<220> FEATURE:
<221> NAME/KEY: modified_base
<222> LOCATION: (23)..(23)
<223> OTHER INFORMATION: 5-propynyl-d-Uracil
<220> FEATURE:
<221> NAME/KEY: modified_base
<222> LOCATION: (25)..(25)
<223> OTHER INFORMATION: 5-propynyl-d-Uracil
<220> FEATURE:
<221> NAME/KEY: modified_base
<222> LOCATION: (27)..(27)
<223> OTHER INFORMATION: 5-methyl-d-Cytosine
<220> FEATURE:
<221> NAME/KEY: modified_base
<222> LOCATION: (30)..(30)
<223> OTHER INFORMATION: 5-propynyl-d-Uracil
<220> FEATURE:
<221> NAME/KEY: modified_base
<222> LOCATION: (31)..(31)
<223> OTHER INFORMATION: 5-methyl-d-Cytosine

<400> SEQUENCE: 27
ccuuaaaauu gucautttta taugugctgu c                                                31

<210> SEQ ID NO 28
<211> LENGTH: 31
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: 5-propynyl-d-Uracil
<220> FEATURE:
<221> NAME/KEY: modified_base
<222> LOCATION: (12)..(12)
<223> OTHER INFORMATION: 5-propynyl-d-Uracil
<220> FEATURE:
<221> NAME/KEY: modified_base
<222> LOCATION: (25)..(25)
<223> OTHER INFORMATION: 5-propynyl-d-Uracil
<220> FEATURE:
<221> NAME/KEY: modified_base
<222> LOCATION: (27)..(27)
<223> OTHER INFORMATION: 5-methyl-d-Cytosine
<220> FEATURE:
<221> NAME/KEY: modified_base
<222> LOCATION: (30)..(30)
<223> OTHER INFORMATION: 5-propynyl-d-Uracil

<400> SEQUENCE: 28
ccttaaaatu gucattttta tatgugctgu c                                                31

<210> SEQ ID NO 29
<211> LENGTH: 31
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: 5-propynyl-d-Uracil
<220> FEATURE:
<221> NAME/KEY: modified_base
<222> LOCATION: (12)..(12)
<223> OTHER INFORMATION: 5-propynyl-d-Uracil
<220> FEATURE:
<221> NAME/KEY: modified_base
<222> LOCATION: (25)..(25)
<223> OTHER INFORMATION: 5-propynyl-d-Uracil
<220> FEATURE:
<221> NAME/KEY: modified_base
<222> LOCATION: (27)..(27)
<223> OTHER INFORMATION: 5-methyl-d-Cytosine
<220> FEATURE:
<221> NAME/KEY: modified_base
<222> LOCATION: (28)..(28)
<223> OTHER INFORMATION: 5-propynyl-d-Uracil
<220> FEATURE:
<221> NAME/KEY: modified_base
<222> LOCATION: (30)..(30)
<223> OTHER INFORMATION: 5-propynyl-d-Uracil

<400> SEQUENCE: 29
ccttaaaatu gucattttta tatguacutu c                                   31

<210> SEQ ID NO 30
<211> LENGTH: 31
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 5-methyl-d-Cytosine
<220> FEATURE:
<221> NAME/KEY: modified_base
<222> LOCATION: (3)..(4)
<223> OTHER INFORMATION: 5-propynyl-d-Uracil
<220> FEATURE:
<221> NAME/KEY: modified_base
<222> LOCATION: (9)..(10)
<223> OTHER INFORMATION: 5-propynyl-d-Uracil
<220> FEATURE:
<221> NAME/KEY: modified_base
<222> LOCATION: (12)..(12)
<223> OTHER INFORMATION: 5-propynyl-d-Uracil
<220> FEATURE:
<221> NAME/KEY: modified_base
<222> LOCATION: (13)..(13)
<223> OTHER INFORMATION: 5-methyl-d-Cytosine
<220> FEATURE:
<221> NAME/KEY: modified_base
<222> LOCATION: (23)..(23)
<223> OTHER INFORMATION: 5-propynyl-d-Uracil
<220> FEATURE:
<221> NAME/KEY: modified_base
<222> LOCATION: (25)..(25)
<223> OTHER INFORMATION: 5-propynyl-d-Uracil
<220> FEATURE:
<221> NAME/KEY: modified_base
<222> LOCATION: (27)..(27)
<223> OTHER INFORMATION: 5-methyl-d-Cytosine
<220> FEATURE:
<221> NAME/KEY: modified_base
<222> LOCATION: (28)..(28)
<223> OTHER INFORMATION: 5-propynyl-d-Uracil
<220> FEATURE:
<221> NAME/KEY: modified_base
<222> LOCATION: (30)..(30)
<223> OTHER INFORMATION: 5-propynyl-d-Uracil

<400> SEQUENCE: 30
ccuuaaaauu gucattttta tauguacutu c                                   31

<210> SEQ ID NO 31
<211> LENGTH: 30
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 5-methyl-d-Cytosine
<220> FEATURE:
<221> NAME/KEY: modified_base
<222> LOCATION: (2)..(3)
<223> OTHER INFORMATION: 5-propynyl-d-Uracil
<220> FEATURE:
<221> NAME/KEY: modified_base

```
<222> LOCATION: (8)..(9)
<223> OTHER INFORMATION: 5-propynyl-d-Uracil
<220> FEATURE:
<221> NAME/KEY: modified_base
<222> LOCATION: (11)..(11)
<223> OTHER INFORMATION: 5-propynyl-d-Uracil
<220> FEATURE:
<221> NAME/KEY: modified_base
<222> LOCATION: (12)..(12)
<223> OTHER INFORMATION: 5-methyl-d-Cytosine
<220> FEATURE:
<221> NAME/KEY: modified_base
<222> LOCATION: (14)..(14)
<223> OTHER INFORMATION: 5-propynyl-d-Uracil
<220> FEATURE:
<221> NAME/KEY: modified_base
<222> LOCATION: (20)..(20)
<223> OTHER INFORMATION: 5-propynyl-d-Uracil
<220> FEATURE:
<221> NAME/KEY: modified_base
<222> LOCATION: (22)..(22)
<223> OTHER INFORMATION: 5-propynyl-d-Uracil
<220> FEATURE:
<221> NAME/KEY: modified_base
<222> LOCATION: (24)..(24)
<223> OTHER INFORMATION: 5-propynyl-d-Uracil
<220> FEATURE:
<221> NAME/KEY: modified_base
<222> LOCATION: (26)..(26)
<223> OTHER INFORMATION: 5-methyl-d-Cytosine
<220> FEATURE:
<221> NAME/KEY: modified_base
<222> LOCATION: (27)..(29)
<223> OTHER INFORMATION: 5-propynyl-d-Uracil
<220> FEATURE:
<221> NAME/KEY: modified_base
<222> LOCATION: (30)..(30)
<223> OTHER INFORMATION: 5-methyl-d-Cytosine

<400> SEQUENCE: 31
cuuaaaauug ucauttttau auguacuuuc                                      30
```

HIGH-RISK HUMAN PAPILLOMAVIRUS DETECTION

CROSS-REFERENCES TO RELATED APPLICATIONS

This application is a divisional of application Ser. No. 12/332,164, filed on Dec. 10, 2008, which is a divisional of application Ser. No. 11/119,343, filed on, Apr. 29, 2005, now U.S. Pat. No. 7,482,142, which claims the benefit of the U.S. Provisional Application No. 60/568,934, filed on May 7, 2004, the disclosures of which are incorporated by reference in their entirety for all purposes.

FIELD OF THE INVENTION

The present invention relates to the fields of molecular biology and nucleic acid chemistry. The invention provides methods and reagents for detecting human papillomavirus and accordingly, also relates to the fields of medical diagnostics and prognostics.

BACKGROUND OF THE INVENTION

Human papillomaviruses (HPVs) are a group of epitheliotropic viruses characterized by a circular, double-stranded DNA genome. Different HPV types infect the skin or the mucosa of the respiratory and anogenital tract, and correlate with benign and malignant neoplasia of cutaneous and mucosal epithelia. To illustrate, HPV DNA is found in essentially all cases of cervical carcinoma and in many precursor lesions. Cervical carcinoma is currently second only to breast cancer as the most prevalent malignancy in women worldwide.

In excess of 100 different HPV types, which are numbered in chronological order of isolation, have been characterized to date. An HPV genome is currently classified as a new type if it has less than 90% DNA sequence homology to other HPVs in the L1 open reading frame. Further, based on the induced benign, premalignant or malignant lesions of the cervix, anogenital HPV is divided into low-risk (including, e.g., types 6, 11, 40, 42, 43, 44, 54, 61, 70, 72, and 81) and high-risk (including, e.g., types 16, 18, 31, 33, 35, 39, 45, 51, 52, 56, 58, 59, 68, 73, and 82) types, respectively. See, e.g., Munoz et al. (2003) "Epidemiologic classification of human papillomavirus types associated with cervical cancer," *N. Engl. J. Med.* 348(6):518-527, which is incorporated by reference. The genome of low-risk HPV types typically remains episomal, while the circular ds-DNA genome of high-risk HPV types may integrate into the human genome as part of carcinogenesis. Moreover, high-risk HPV types account for more than 80% of all invasive cervical cancers. As a consequence, the detection and identification of particular HPV types present in patient samples provides significant diagnostic and prognostic information.

Various approaches to the diagnosis of HPV infections have been attempted. Culture-based techniques have generally proven to be unfeasible. Immunoassays directed at HPV detection are typically limited by insufficient sensitivity and specificity. The most successful methods of diagnosing HPV infections typically involve nucleic acid hybridization-based assays with or without the amplification of target HPV DNA sequences.

Many hybridization-based diagnostic tests lack sufficient specificity to differentiate between high-and low-risk HPV types or to distinguish between various high-risk HPV types. This can lead to biased assay results, including false positives. One consequence of such misdiagnosis may be the administration of an inappropriate course of treatment to a patient.

SUMMARY OF THE INVENTION

The present invention provides methods and reagents for the rapid detection of HPV. For example, the invention provides cross-reactive oligonucleotides for the detection of various high-risk HPVs, including HPV31, HPV33, HPV35, HPV52, HPV56, and/or HPV58. In addition to compositions and reaction mixtures, the invention also relates to kits and systems for detecting these pathogenic agents, and to related computer and computer readable media.

In one aspect, the invention provides an oligonucleotide consisting of a nucleic acid with a sequence selected from the group consisting of: SEQ ID NOS: 1-31 and complements thereof. In another aspect, the invention provides an oligonucleotide comprising a nucleic acid with a sequence selected from the group consisting of: SEQ ID NOS: 1-31 and complements thereof, which oligonucleotide consists of 100 or fewer nucleotides. In still another aspect, the invention relates to an oligonucleotide comprising a nucleic acid having at least 90% sequence identity to one of SEQ ID NOS: 1-31 or a complement thereof, which oligonucleotide consists of 100 or fewer nucleotides. In some embodiments, the nucleic acid has at least 95% sequence identity to one of SEQ ID NOS: 1-31 or the complement thereof. In certain embodiments, the nucleic acid comprises at least one modified nucleotide substitution (e.g., between about two and about 20 modified nucleotide substitutions).

In another aspect, the invention relates to a composition comprising a sample (e.g., derived from a subject) and at least one oligonucleotide that comprises a nucleic acid with a sequence selected from the group consisting of: SEQ ID NOS: 1-31, a substantially identical variant thereof in which the variant has at least 90% sequence identity to one of SEQ ID NOS: 1-31, and complements of SEQ ID NOS: 1-31 and the variant, which oligonucleotide consists of 100 or fewer nucleotides.

The oligonucleotides of the compositions described herein are provided in various formats. In certain embodiments, for example, at least one of the oligonucleotides is in solution. In some embodiments, a solid support comprises the oligonucleotide. Optionally, the oligonucleotide is non-covalently or covalently attached to the solid support. Exemplary solid supports utilized in these embodiments are optionally selected from, e.g., a plate, a microwell plate, a bead, a microbead, a fiber, a whisker, a comb, a hybridization chip, a membrane, a single crystal, a ceramic layer, a self-assembling monolayer, and the like. In certain embodiments, a linker attaches the oligonucleotide to the solid support. The linker is optionally selected from, e.g. an oligopeptide, an oligonucleotide, an oligopolyamide, an oligoethyleneglycerol, an oligoacrylamide, an alkyl chain, and/or the like. To further illustrate, the oligonucleotide is optionally bovine serum albumin-conjugated. In some embodiments, a cleavable attachment attaches the oligonucleotide to the solid support. For example, the cleavable attachment is typically cleavable by heat, an enzyme, a chemical agent, electromagnetic radiation, or the like.

In another aspect, the invention provides a method of determining a presence of at least one high-risk human papillomavirus (HPV) type in a sample. The method includes (a) contacting nucleic acids and/or amplicons thereof from the sample with at least one oligonucleotide that comprises a nucleic acid with a sequence selected from the group consisting of: SEQ ID NOS: 1-31 and complements of SEQ ID NOS:

1-31, which oligonucleotide consists of 100 or fewer nucleotides. The method also includes (b) monitoring binding between the nucleic acids and/or amplicons thereof, and the oligonucleotide, in which detectable binding between the nucleic acids and/or amplicons thereof, and the oligonucleotide, determines the presence of the high-risk HPV type in the sample.

In still another aspect, the invention relates to a method of determining a presence of at least one high-risk human papillomavirus (HPV) type in a sample. The method includes (a) contacting nucleic acids and/or amplicons thereof from the sample with at least one oligonucleotide that comprises a nucleic acid having at least 90% sequence identity to one of SEQ ID NOS: 1-31 and complements of SEQ ID NOS: 1-31, which oligonucleotide consists of 100 or fewer nucleotides. Typically, the sample is derived from a human subject. The method also includes (b) monitoring binding between the nucleic acids and/or amplicons thereof, and the oligonucleotide, in which detectable binding between the nucleic acids and/or amplicons thereof, and the oligonucleotide, determines the presence of the high-risk HPV type (e.g., HPV31, HPV33, HPV35, HPV52, HPV56, and/or HPV58) in the sample. In certain embodiments, for example, (b) comprises monitoring binding between the oligonucleotide and the nucleic acid and/or amplicons thereof, if any, under stringent hybridization conditions. Optionally, the method comprises repeating (a) and (b) at least once using at least one additional sample and comparing the binding between the nucleic acids and/or amplicons thereof, and the oligonucleotide, of (b) with at least one repeated (b). In some embodiments, the nucleic acids and/or amplicons thereof and the oligonucleotide are contacted in solution. In certain embodiments, a solid support comprises the nucleic acids and/or amplicons thereof, whereas in others, a solid support comprises the oligonucleotide.

In certain embodiments, at least one segment of the nucleic acids is amplified prior to or during (a) using at least one nucleic acid amplification technique to produce the amplicons and (b) comprises monitoring the binding between the nucleic acids and/or amplicons thereof, and the oligonucleotide, during or after amplification. In these embodiments, the nucleic acid amplification technique utilizes at least one primer nucleic acid that comprises at least one labeling moiety.

In some embodiments, the nucleic acids and/or amplicons thereof, and/or the oligonucleotide comprises at least one labeling moiety (e.g., a fluorescent labeling moiety, etc.) and/or at least one quencher moiety. In these embodiments, (b) comprises detecting a detectable signal produced by the labeling moiety. Optionally, (b) comprises: (i) amplifying a detectable signal produced by the labeling moiety to produce an amplified signal, and (ii) detecting the amplified signal.

In another aspect, the invention provides a kit that includes (a) at least one oligonucleotide that comprises a nucleic acid with a sequence selected from the group consisting of: SEQ ID NOS: 1-31, a substantially identical variant thereof in which the variant has at least 90% sequence identity to one of SEQ ID NOS: 1-31, and complements of SEQ ID NOS: 1-31 and the variant, which oligonucleotide consists of 100 or fewer nucleotides. The kit also includes (b) instructions for determining a presence of at least one high-risk human papillomavirus (HPV) type (e.g., HPV31, HPV33, HPV35, HPV52, HPV56, and/or HPV58) in a sample by monitoring binding between nucleic acids and/or amplicons thereof from the sample and the oligonucleotide. In some embodiments, the oligonucleotide is in solution. In other embodiments, a solid support (e.g., a plate, a microwell plate, a bead, a microbead, a fiber, a whisker, a comb, a hybridization chip, a membrane, a single crystal, a ceramic layer, a self-assembling monolayer, etc.) comprises the oligonucleotide. Optionally, the kit further includes (c) at least one container for packaging the oligonucleotide and/or the instructions. In some embodiments, the kit further comprises instructions for obtaining samples.

In certain embodiments, the kit further includes at least one primer nucleic acid that is at least partially complementary to at least one segment of an L1 region of the high-risk HPV type. In these embodiments, the kit optionally further includes instructions for amplifying one or more segments of the L1 region with the primer nucleic acid, at least one nucleotide incorporating biocatalyst, and one or more nucleotides. The primer nucleic acid optionally comprises at least one labeling moiety. In some of these embodiments, the kit further includes at least one nucleotide incorporating biocatalyst (e.g., a polymerase, a ligase, etc.) and/or one or more nucleotides.

In one aspect, the invention provides a system for detecting at least one high-risk human papillomavirus (HPV) type (e.g., HPV31, HPV33, HPV35, HPV52, HPV56, and/or HPV58) in a sample. The system includes (a) at least one oligonucleotide that comprises a nucleic acid with a sequence selected from the group consisting of: SEQ ID NOS: 1-31, a substantially identical variant thereof in which the variant has at least 90% sequence identity to one of SEQ ID NOS: 1-31, and complements of SEQ ID NOS: 1-31 and the variant, which oligonucleotide consists of 100 or fewer nucleotides. The system also includes (b) at least one detector that detects binding between nucleic acids and/or amplicons thereof from the sample and the oligonucleotide. In addition, the system also includes (c) at least one controller operably connected to the detector, which controller comprises one or more instructions sets that correlate the binding detected by the detector with a presence of the high-risk HPV type in the sample. In certain embodiments, at least one container or solid support comprises the oligonucleotide. In some of these embodiments, the system further includes (d) at least one thermal modulator operably connected to the container or solid support to modulate temperature in the container or on the solid support, and/or (e) at least one fluid transfer component that transfers fluid to and/or from the container or solid support.

In another aspect, the invention provides a system that includes (a) computer or computer readable medium comprising a data set that comprises at least one character string that corresponds to at least one sequence selected from the group consisting of: SEQ. ID NOS. 1-31 and complements thereof. The system also includes (b) an automatic synthesizer coupled to an output of the computer or computer readable medium, which automatic synthesizer accepts instructions from the computer or computer readable medium, which instructions direct synthesis of one or more nucleic acids that correspond to one or more character strings in the data set.

The oligonucleotides, including those provided for in the compositions, methods, kits, and systems described herein, include various embodiments. In some embodiments, for example, variants have at least 90% sequence identity to one of SEQ ID NOS: 1-31 and complements thereof, whereas in others, the variants have at least 95% sequence identity to one of SEQ ID NOS: 1-31 and complements thereof. In certain embodiments, the sequence of the nucleic acid comprises at least one modified nucleotide substitution, e.g., such that the oligonucleotide comprises a substantially identical variant having at least 90% sequence identity to one of SEQ ID NOS: 1-31. For example, the sequence of the nucleic acid optionally comprises at least one nucleotide mismatch with a substantially complementary sequence in an L1 region of at least one high-risk human papillomavirus (HPV) type. In these embodiments, the modified nucleotide substitution is typically positioned proximal to the nucleotide mismatch. To illustrate, the sequence of the nucleic acid optionally comprises between about two and about 20 modified nucleotide substitutions. The modified nucleotide substitution generally modifies a melting temperature ($T_m$) of the oligonucleotide by at least about 0.2° C. relative to a $T_m$ of a corresponding unmodified oligonucleotide. Optionally, the modified nucleotide is selected from, e.g., a C5-methyl-dC, a C5-ethyl-dC, a C5-methyl-dU, a C5-ethyl-dU, a 2,6-diaminopurine, a C5-propynyl-dC, a C5-propynyl-dU, a C7-propynyl-dA, a C7-propynyl-dG, a C5-propargylamino-dC, a C5-propargylamino-dU, a C7-propargylamino-dA, a C7-propargylamino-dG, a 7-deaza-2-deoxyxanthosine, a pyrazolopyrimidine analog, a pseudo-dU, a nitro pyrrole, a nitro indole, 2'-0-methyl Ribo-U, 2'-0-methyl Ribo-C, an 8-aza-dA, an 8-aza-dG, a 7-deaza-dA, a 7-deaza-dG, an N4-ethyl-dC, an N6-methyl-dA, or the like. In some embodiments, the oligonucleotide includes at least one labeling moiety and/or at least one quencher moiety. For example, the labeling moiety optionally comprises bovine serum albumin, a fluorescent dye, a weakly fluorescent label, a non-fluorescent label, a colorimetric label, a chemiluminescent label, a bioluminescent label, an antibody, an antigen, biotin, a hapten, a mass-modifying group, a radioisotope, an enzyme, or the like.

DETAILED DESCRIPTION

I. Definitions

Figure 1:
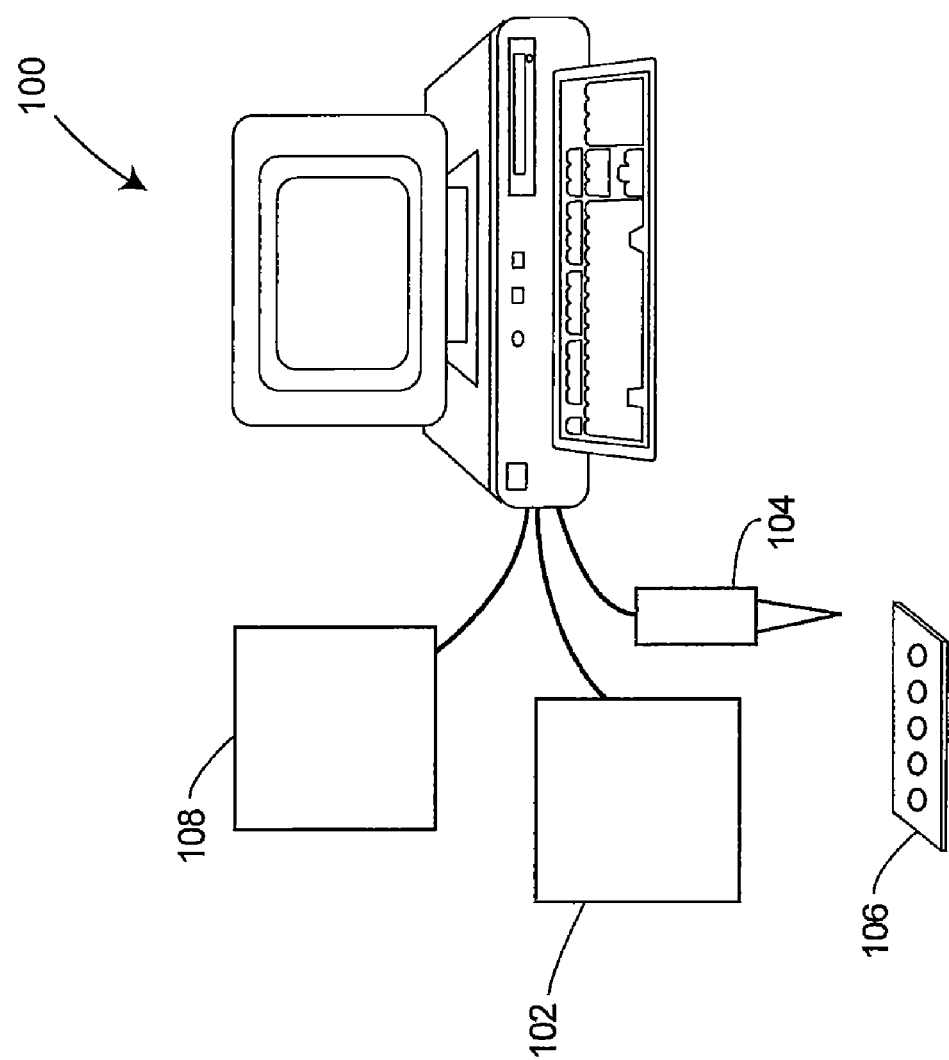
FIG. 1 is a block diagram showing a representative example system for detecting HPV in a sample.

Before describing the present invention in detail, it is to be understood that this invention is not limited to particular oligonucleotides, methods, compositions, kits, systems, computers, or computer readable media, which can, of course, vary. It is also to be understood that the terminology used herein is for the purpose of describing particular embodiments only, and is not intended to be limiting. Further, unless defined otherwise, all technical and scientific terms used herein have the same meaning as commonly understood by one of ordinary skill in the art to which this invention pertains. In describing and claiming the present invention, the following terminology and grammatical variants will be used in accordance with the definitions set forth below.

A "5'-nuclease probe" refers to an oligonucleotide that comprises at least two labels and emits radiation of increased intensity after one of the two labels is cleaved or otherwise separated from the oligonucleotide. In certain embodiments, for example, a 5'-nuclease probe is labeled with two different fluorescent dyes, e.g., a 5' terminus reporter dye and the 3' terminus quencher dye or moiety. In some embodiments, 5'-nuclease probes are labeled at one or more positions other than, or in addition to, terminal positions. When the probe is intact, energy transfer typically occurs between the two fluorophores such that fluorescent emission from the reporter dye is quenched. During an extension step of a polymerase chain reaction, for example, a 5'-nuclease probe bound to a template nucleic acid is cleaved by the 5' nuclease activity of, e.g., a Taq polymerase such that the fluorescent emission of the reporter dye is no longer quenched. Exemplary 5'-nuclease probes are described in, e.g., U.S. Pat. No. 5,210,015, entitled "HOMOGENEOUS ASSAY SYSTEM USING THE NUCLEASE ACTIVITY OF A NUCLEIC ACID POLYMERASE," issued May 11, 1993 to Gelfand et al., U.S. Pat. No. 5,994,056, entitled "HOMOGENEOUS METHODS FOR NUCLEIC ACID AMPLIFICATION AND DETECTION," issued Nov. 30, 1999 to Higuchi, and U.S. Pat. No. 6,171,785, entitled "METHODS AND DEVICES FOR HEMOGENEOUS NUCLEIC ACID AMPLIFICATION AND DETECTOR," issued Jan. 9, 2001 to Higuchi, which are each incorporated by reference.

The term "alteration" refers to a change in a nucleic acid sequence, including, but not limited to, a substitution, an insertion, and/or a deletion. For example, a variant nucleic acid typically comprises one or more alterations relative to a corresponding non-variant nucleic acid.

An "amplicon" refers to a molecule made by copying or transcribing another molecule, e.g., as occurs in transcription, cloning, and/or in a polymerase chain reaction ("PCR") (e.g., strand displacement PCR amplification (SDA), duplex PCR amplification, etc.) or other nucleic acid amplification technique. Typically, an amplicon is a copy of a selected nucleic acid (e.g., a template or target nucleic acid) or is complementary thereto.

An "amplification reaction" refers to a primer initiated replication of one or more target nucleic acid sequences or complements thereto.

An "amplified signal" refers to an increased detectable signal that can be produced in the absence of, or in conjunction with, a nucleic acid amplification reaction. Exemplary signal amplification techniques are described in, e.g., Cao et al. (1995) "Clinical evaluation of branched DNA signal amplification for quantifying HIV type 1 in human plasma," *AIDS Res Hum Retroviruses* 11(3):353-361, and in U.S. Pat. No. 5,437,977 to Segev, U.S. Pat. No. 6,033,853 to Delair et al., and U.S. Pat. No. 6,180,777 to Horn, which are each incorporated by reference.

An "array" refers to an assemblage of elements. The assemblage can be spatially ordered (a "patterned array") or disordered (a "randomly patterned" array). The array can form or comprise one or more functional elements (e.g., a probe region on a microarray) or it can be non-functional.

The term "attached" or "conjugated" refers to interactions and/or states including, but not limited to, covalent bonding, ionic bonding, chemisorption, physisorption, and combinations thereof. In certain embodiments, for example, oligonucleotides are attached to solid supports. In some of these embodiments, an oligonucleotide is conjugated with biotin (i.e., is biotinylated) and a solid support is conjugated with avidin such that the oligonucleotide attaches to the solid support via the binding interaction of, e.g., biotin and avidin.

A "character" when used in reference to a character of a character string refers to a subunit of the string. In one embodiment, the character of a character string encodes one subunit of an encoded biological molecule. Thus, for example, where the encoded biological molecule is a polynucleotide or oligonucleotide, a character of the string encodes a single nucleotide.

A "character string" is any entity capable of storing sequence information (e.g., the subunit structure of a biological molecule such as the nucleotide sequence of a nucleic acid, etc.). In one embodiment, the character string can be a simple sequence of characters (letters, numbers, or other symbols) or it can be a numeric or coded representation of such information in tangible or intangible (e.g., electronic, magnetic, etc.) form. The character string need not be "linear," but can also exist in a number of other forms, e.g., a linked list or other non-linear array (e.g., used as a code to generate a linear array of characters), or the like. Character strings are typically those which encode oligonucleotide or polynucleotide strings, directly or indirectly, including any encrypted strings, or images, or arrangements of objects which can be transformed unambiguously to character strings representing sequences of monomers or multimers in polynucleotides, or the like (whether made of natural or artificial monomers).

The term "cleavage" in the context of solid supports refers to a process of releasing a material or compound from a solid support to permit analysis of the compound by solution-phase methods. See, e.g., Wells et al. (1998) "Cleavage and Analysis of Material from Single Resin Beads," *J. Org. Chem.* 63:6430, which is incorporated by reference. In certain other contexts, such as 5'-nuclease assays or reactions, 5'-nuclease probes can be cleaved by the nuclease activity associated with various nucleic acid polymerases typically utilized in those reactions.

The term "complement thereof" refers to nucleic acid that is both the same length as, and exactly complementary to, a given nucleic acid.

A "composition" refers to a combination of two or more different components. In certain embodiments, for example, a composition includes a solid support that comprises one or more oligonucleotides, e.g., covalently or non-covalently attached to a surface of the support. In other embodiments, a composition includes one or more oligonucleotides in solution.

Two nucleic acids "correspond" when they have substantially identical or complementary sequences. In certain embodiments, for example, two nucleic acids correspond to one another when the sequence of one nucleic acid is derived naturally or artificially from the other. To further illustrate, a substantially identical variant of a nucleic acid includes one or more modified nucleotide substitutions relative to a corresponding unmodified nucleic acid in some embodiments of the invention.

An oligonucleotide is "cross-reactive" when it is capable of selectively hybridizing to two or more target nucleic acids under suitable conditions to permit detection of those target nucleic acids.

The term "deletion" in the context of a nucleic acid sequence refers to an alteration in which at least one nucleotide is removed from the nucleic acid sequence, e.g., from a 5'-terminus, from a 3'-terminus, and/or from an internal position of the nucleic acid sequence.

The term "derivative" refers to a chemical substance related structurally to another substance, or a chemical substance that can be made from another substance (i.e., the substance it is derived from), e.g., through chemical or enzymatic modification. To illustrate, oligonucleotides are optionally conjugated with biotin or a biotin derivative. To further illustrate, one nucleic acid can be "derived" from another through processes, such as chemical synthesis based on knowledge of the sequence of the other nucleic acid, amplification of the other nucleic acid, or the like.

The term "detectably bind" and "detectable binding" refers to binding between at least two molecular species (e.g., a probe nucleic acid and a target nucleic acid) that is detectable above a background signal (e.g., noise) using one or more methods of detection.

Nucleic acids are "extended" or "elongated" when additional nucleotides (or other analogous molecules) are incorporated into the nucleic acids. For example, a nucleic acid is optionally extended by a nucleotide incorporating biocatalyst, such as a polymerase that typically adds nucleotides at the 3' terminal end of a nucleic acid.

An "extended primer nucleic acid" refers to a primer nucleic acid to which one or more additional nucleotides have been added or otherwise incorporated (e.g., covalently bonded thereto).

A "genotype" or "type" refers to all or part of the genetic constitution of a virus, a cell, or subject. For example, the cross-reactive oligonucleotides of the invention bind to multiple high-risk HPV types (selected from, e.g., HPV31, HPV33, HPV35, HPV52, HPV56, and/or HPV58) under selected conditions.

The term "high risk human papillomavirus type" or "high risk HPV type" refers types of anogenital HPV that are considered to be carcinogenic. Examples of high risk HPV types include 16, 18, 31, 33, 35, 39, 45, 51, 52, 56, 58, 59, 68, 73, and 82. HPV classification is also described in, e.g., Munoz et al. (2003) "Epidemiologic classification of human papillomavirus types associated with cervical cancer," *N. Engl. J. Med.* 348(6):518-527, which is incorporated by reference.

The term "human papillomavirus" or "HPV" refers to a double-stranded DNA virus of the family Papovaviridae, genus *Papillomavirus* that infects human hosts. To date, over 100 types of HPV have been identified. Additional general description of HPV is provided in, e.g., zur Hausen (2002) "Papillomaviruses and cancer: from basic studies to clinical application," *Nat Rev Cancer.* 2(5):342-350, Stern et al. (Eds.), *Human Papillomaviruses and Cervical Cancer: Biology and Immunology*, Oxford University Press (1994), Sterling et al. (Eds.), *Human Papillomaviruses: Clinical and Scientific Advances*, Arnold Publications Series, Oxford University Press (2002), Guo, *Molecular Mechanisms in Cervical Carcinogenesis Studies of Clonality, Somatic Genetic Alterations and Human Papillomavirus Variants in Cervical Pre-Invasive and Invasive Cancer*, Uppsala University Press (2000), and Syrjanen et al., *Papillomavirus Infections in Human Pathology*, John Wiley & Sons, Inc. (1999), which are each incorporated by reference. See also, the HPV Sequence Database provided on the world wide web at hpv-web.lanl.gov as of May 7, 2004.

The term "human papillomavirus nucleic acid" or "HPV nucleic acid" refers to a nucleic acid that is derived or isolated from a human papillomavirus and/or an amplicon of such a nucleic acid.

"Stringent hybridization wash conditions" in the context of nucleic acid hybridization assays or experiments, such as nucleic acid amplification reactions, Southern and northern hybridizations, or the like, are sequence dependent, and are different under different environmental parameters. An extensive guide to the hybridization of nucleic acids is found in Tijssen (1993), supra. and in Hames and Higgins, 1 and 2.

For purposes of the present invention, "highly stringent" hybridization and wash conditions are selected to be at least about 5° C. lower than the thermal melting point ($T_m$) for the specific sequence at a defined ionic strength and pH. The $T_m$ is the temperature (under defined ionic strength and pH) at which 50% of the test sequence hybridizes to a perfectly matched probe. Very stringent conditions are selected to be equal to the $T_m$ for a particular probe.

An example of stringent hybridization conditions for hybridization of complementary nucleic acids on a filter in a Southern or northern blot is 50% formalin with 1 mg of heparin at 42° C., with the hybridization being carried out overnight. An example of stringent wash conditions is a 0.2× SSC wash at 65° C. for 15 minutes (see, Sambrook et al., *Molecular Cloning: A Laboratory Manual*, 3rd Ed., Cold Spring Harbor Laboratory Press, Cold Spring Harbor, N.Y. (2001), which is incorporated by reference, for a description of SSC buffer). Often the high stringency wash is preceded by a low stringency wash to remove background probe signal. An example low stringency wash is 2×SSC at 40° C. for 15 minutes. In general, a signal to noise ratio of 5× (or higher) than that observed for an unrelated probe in the particular hybridization assay indicates detection of a specific hybridization.

Comparative hybridization can be used to identify nucleic acids of the invention.

In particular, detection of stringent hybridization in the context of the present invention indicates strong structural similarity to, e.g., the nucleic acids provided in the sequence listing herein. For example, it is desirable to identify test nucleic acids that hybridize to the exemplar nucleic acids herein under stringent conditions. One measure of stringent hybridization is the ability to detectably hybridize to one of the listed nucleic acids (e.g., nucleic acids with sequences selected from SEQ ID NOS: 1-31 and complements thereof) under stringent conditions. Stringent hybridization and wash conditions can easily be determined empirically for any test nucleic acid.

For example, in determining highly stringent hybridization and wash conditions, the stringency of the hybridization and wash conditions are gradually increased (e.g., by increasing temperature, decreasing salt concentration, increasing detergent concentration and/or increasing the concentration of organic solvents such as formalin in the hybridization or wash), until a selected set of criteria is met. For example, the stringency of the hybridization and wash conditions are gradually increased until an oligonucleotide consisting of or comprising one or more nucleic acid sequences selected from SEQ ID NOS: 1-31 and complementary oligonucleotide sequences thereof, binds to a perfectly matched complementary target (again, a nucleic acid comprising one or more nucleic acid sequences selected from SEQ ID NOS: 1-31 and complementary oligonucleotide sequences thereof), with a signal to noise ratio that is at least 5× as high as that observed for hybridization of the oligonucleotide to a non-target nucleic acid. In this case, non-target nucleic acids are those from low-risk HPV types or organisms other than HPV. Examples of such non-target nucleic acids include, e.g., the L1 region of HPV types 6, 11, 26, 40, 42, 43, 44, 53, 54, 55, 57, 64, 66, 67, and 70. Additional such sequences can be identified in, e.g., GenBank® by one of skill in the art.

The detection of target nucleic acids which hybridize to the nucleic acids represented by SEQ ID NOS: 1-31 and complements thereof under high stringency conditions are a feature of the invention. Examples of such nucleic acids include those with one or a few silent or conservative nucleic acid substitutions as compared to a given nucleic acid sequence.

The terms "identical" or percent "identity" in the context of two or more nucleic acid sequences, refer to two or more sequences or subsequences that are the same or have a specified percentage of nucleotides that are the same, when compared and aligned for maximum correspondence, e.g., as measured using one of the sequence comparison algorithms available to persons of skill or by visual inspection. Exemplary algorithms that are suitable for determining percent sequence identity and sequence similarity are the BLAST programs, which are described in, e.g., Altschul et al. (1990) "Basic local alignment search tool" *J. Mol. Biol.* 215:403-410, Gish et al. (1993) "Identification of protein coding regions by database similarity search" *Nature Genet.* 3:266-272, Madden et al. (1996) "Applications of network BLAST server" *Meth. Enzymol.* 266:131-141, Altschul et al. (1997) "Gapped BLAST and PSI-BLAST: a new generation of protein database search programs" *Nucleic Acids Res.* 25:3389-3402, and Zhang et al. (1997) "PowerBLAST: A new network BLAST application for interactive or automated sequence analysis and annotation" *Genome Res.* 7:649-656, which are each incorporated by reference.

The phrase "in solution" refers to an assay or reaction condition in which the components of the assay or reaction are not attached to a solid support. For example, certain assays of the invention include incubating oligonucleotides together with HPV nucleic acids and HPV nucleic acid amplicons in solution to allow hybridization to occur.

The term "insertion" in the context of a nucleic acid sequence refers to an alteration in which at least one nucleotide is added to the nucleic acid sequence, e.g., at a 5'-terminus, at a 3'-terminus, and/or at an internal position of the nucleic acid sequence.

The "L1 region" refers to the L1 open reading frame of the human papillomavirus genome.

A "label" or "labeling moiety" refers to a moiety attached (covalently or non-covalently), or capable of being attached, to a molecule, which moiety provides or is capable of providing information about the molecule (e.g., descriptive, identifying, etc. information about the molecule) or another molecule with which the labeled molecule interacts (e.g., hybridizes, etc.). Exemplary labels include fluorescent labels (including, e.g., quenchers or absorbers), weakly fluorescent labels, non-fluorescent labels, colorimetric labels, chemiluminescent labels, bioluminescent labels, radioactive labels, mass-modifying groups, antibodies, antigens, biotin, haptens, enzymes (including, e.g., peroxidase, phosphatase, etc.), and the like.

A "linker" refers to a chemical moiety that covalently or non-covalently attaches a compound or substituent group to another moiety, e.g., a nucleic acid, an oligonucleotide probe, a primer nucleic acid, an amplicon, a solid support, or the like. For example, linkers are optionally used to attach oligonucleotides to a solid support (e.g., in a linear or other logical oligonucleotide array). To further illustrate, a linker optionally attaches a label (e.g., a fluorescent dye, a radioisotope, etc.) to an oligonucleotide, a primer nucleic acid, or the like. Linkers are typically at least bifunctional chemical moieties and in certain embodiments, they comprise cleavable attachments, which can be cleaved by, e.g., heat, an enzyme, a chemical agent, electromagnetic radiation, etc. to release materials or compounds from, e.g., a solid support. A careful choice of linker allows cleavage to be performed under appropriate conditions compatible with the stability of the compound and assay method. Generally a linker has no specific biological activity other than to, e.g., join chemical species together or to preserve some minimum distance or other spatial relationship between such species. However, the constituents of a linker may be selected to influence some property of the linked chemical species such as three-dimensional conformation, net charge, hydrophobicity, etc. Exemplary linkers include, e.g., oligopeptides, oligonucleotides, oligopolyamides, oligoethyleneglycerols, oligoacrylamides, alkyl chains, or the like. Additional description of linker molecules is provided in, e.g., Hermanson, *Bioconjugate Techniques*, Elsevier Science (1996), Lyttle et al. (1996)

*Nucleic Acids Res.* 24(14):2793, Shchepino et al. (2001) *Nucleosides, Nucleotides, & Nucleic Acids* 20:369, Doronina et al (2001) *Nucleosides, Nucleotides, & Nucleic Acids* 20:1007, Trawick et al. (2001) *Bioconjugate Chem.* 12:900, Olejnik et al. (1998) *Methods in Enzymology* 291:135, and Pljevaljcic et al. (2003) *J. Am. Chem. Soc.* 125(12):3486, all of which are incorporated by reference.

A "mass modifying" group modifies the mass, typically measured in terms of molecular weight as daltons, of a molecule that comprises the group.

A "mixture" refers to a combination of two or more different components. A "reaction mixture" refers a mixture that comprises molecules that can participate in and/or facilitate a given reaction. An "amplification reaction mixture" refers to a solution containing reagents necessary to carry out an amplification reaction, and typically contains primers, a thermostable DNA polymerase, dNTPs, and a divalent metal cation in a suitable buffer. A reaction mixture is referred to as complete if it contains all reagents necessary to carry out the reaction, and incomplete if it contains only a subset of the necessary reagents. It will be understood by one of skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of skill in the art that reaction components are packaged separately for commercialization and that useful commercial kits may contain any subset of the reaction components which includes the modified primers of the invention.

A "modified nucleotide substitution" in the context of an oligonucleotide refers to an alteration in which at least one nucleotide of the oligonucleotide sequence is replaced by a different nucleotide that provides a desired property to the oligonucleotide. Exemplary modified nucleotides that can be substituted in the oligonucleotides described herein include, e.g., a C5-methyl-dC, a C5-ethyl-dC, a C5-methyl-dU, a C5-ethyl-dU, a 2,6-diaminopurine, a C5-propynyl-dC, a C5-propynyl-dU, a C7-propynyl-dA, a C7-propynyl-dG, a C5-propargylamino-dC, a C5-propargylamino-dU, a C7-propargylamino-dA, a C7-propargylamino-dG, a 7-deaza-2-deoxyxanthosine, a pyrazolopyrimidine analog, a pseudo-dU, a nitro pyrrole, a nitro indole, 2'-0-methyl Ribo-U, 2'-0-methyl Ribo-C, an N4-ethyl-dC, an N6-methyl-dA, and the like. Many other modified nucleotides that can be substituted in the oligonucleotides of the invention are referred to herein or are otherwise known in the art. In certain embodiments, modified nucleotide substitutions modify melting temperatures ($T_m$) of the oligonucleotides relative to the melting temperatures of corresponding unmodified oligonucleotides. To further illustrate, certain modified nucleotide substitutions can reduce non-specific nucleic acid amplification (e.g., minimize primer dimer formation or the like), increase the yield of an intended target amplicon, and/or the like in some embodiments of the invention. Examples of these types of nucleic acid modifications are described in, e.g., U.S. Pat. No. 6,001,611, entitled "MODIFIED NUCLEIC ACID AMPLIFICATION PRIMERS," issued Dec. 14, 1999 to Will, which is incorporated by reference.

A "moiety" or "group" refers to one of the portions into which something, such as a molecule, is divided (e.g., a functional group, substituent group, or the like). For example, an oligonucleotide optionally comprises a quencher moiety, a labeling moiety, or the like.

The term "nucleic acid" refers to nucleotides (e.g., ribonucleotides, deoxyribonucleotides, dideoxynucleotides, etc.) and polymers that comprise such nucleotides covalently linked together, either in a linear or branched fashion. Exemplary nucleic acids include deoxyribonucleic acids (DNAs), ribonucleic acids (RNAs), DNA-RNA hybrids, oligonucleotides, polynucleotides, genes, cDNAs, aptamers, antisense nucleic acids, molecular beacons, nucleic acid probes, peptide nucleic acids (PNAs), locked nucleic acids (LNA™s), PNA-DNA conjugates, PNA-RNA conjugates, LNA™-DNA conjugates, LNA™-RNA conjugates, and the like.

A nucleic acid is typically single-stranded or double-stranded and will generally contain phosphodiester bonds, although in some cases, as outlined herein, nucleic acid analogs are included that may have alternate backbones, including, for example and without limitation, phosphoramide (Beaucage et al. (1993) *Tetrahedron* 49(10):1925 and the references therein; Letsinger (1970) *J. Org. Chem.* 35:3800; Sprinzl et al. (1977) *Eur. J. Biochem.* 81:579; Letsinger et al. (1986) *Nucl. Acids Res.* 14: 3487; Sawai et al. (1984) *Chem. Lett.* 805; Letsinger et al. (1988) *J. Am. Chem. Soc.* 110:4470; and Pauwels et al. (1986) *Chemica Scripta* 26:1419), phosphorothioate (Mag et al. (1991) *Nucleic Acids Res.* 19:1437 and U.S. Pat. No. 5,644,048), phosphorodithioate (Briu et al. (1989) *J. Am. Chem. Soc.* 111:2321), O-methylphosphoroamidite linkages (Eckstein, *Oligonucleotides and Analogues: A Practical Approach*, Oxford University Press (1992)), and peptide nucleic acid backbones and linkages (Egholm (1992) *J. Am. Chem. Soc.* 114:1895; Meier et al. (1992) *Chem. Int. Ed. Engl.* 31:1008; Nielsen (1993) *Nature* 365:566; and Carlsson et al. (1996) *Nature* 380:207), which references are each incorporated by reference. Other analog nucleic acids include those with positively charged backbones (Denpcy et al. (1995) *Proc. Natl. Acad. Sci. USA* 92:6097); non-ionic backbones (U.S. Pat. Nos. 5,386,023, 5,637,684, 5,602,240, 5,216,141 and 4,469,863; Angew (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghvi and P. Dan Cook; Mesmaeker et al. (1994) *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghvi and P. Dan Cook, which references are each incorporated by reference. Nucleic acids containing one or more carbocyclic sugars are also included within the definition of nucleic acids (Jenkins et al. (1995) *Chem. Soc. Rev.* pp 169-176, which is incorporated by reference). Several nucleic acid analogs are also described in, e.g., Rawls, *C & E News* Jun. 2, 1997 page 35, which is incorporated by reference. These modifications of the ribose-phosphate backbone may be done to facilitate the addition of additional moieties such as labeling moieties, or to alter the stability and half-life of such molecules in physiological environments.

In addition to naturally occurring heterocyclic bases that are typically found in nucleic acids (e.g., adenine, guanine, thymine, cytosine, and uracil), nucleic acid analogs also include those having non-naturally occurring heterocyclic or other modified bases, many of which are described, or otherwise referred to, herein. In particular, many non-naturally occurring bases are described further in, e.g., Seela et al. (1991) *Helv. Chim. Acta* 74:1790, Grein et al. (1994) *Bioorg. Med. Chem. Lett.* 4:971-976, and Seela et al. (1999) *Helv.*

*Chim. Acta* 82:1640, which are each incorporated by reference. To further illustrate, certain bases used in nucleotides that act as melting temperature ($T_m$) modifiers are optionally included. For example, some of these include 7-deazapurines (e.g., 7-deazaguanine, 7-deazaadenine, etc.), pyrazolo[3,4-d] pyrimidines, propynyl-dN (e.g., propynyl-dU, propynyl-dC, etc.), and the like. See, e.g., U.S. Pat. No. 5,990,303, entitled "SYNTHESIS OF 7-DEAZA-2'-DEOXYGUANOSINE NUCLEOTIDES," which issued Nov. 23, 1999 to Seela, which is incorporated by reference. Other representative heterocyclic bases include, e.g., hypoxanthine, inosine, xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytosine; 5-fluorocytosine; 5-chlorocytosine; 5-iodocytosine; 5-bromocytosine; 5-methylcytosine; 5-propynylcytosine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil, and the like.

Additional examples of modified bases and nucleotides are also described in, e.g., U.S. Pat. No. 5,484,908, entitled "OLIGONUCLEOTIDES CONTAINING 5-PROPYNYL PYRIMIDINES," issued Jan. 16, 1996 to Froehler et al., U.S. Pat. No. 5,645,985, entitled "ENHANCED TRIPLE-HELIX AND DOUBLE-HELIX FORMATION WITH OLIGOMERS CONTAINING MODIFIED PYRIMIDINES," issued Jul. 8, 1997 to Froehler et al., U.S. Pat. No. 5,830,653, entitled "METHODS OF USING OLIGOMERS CONTAINING MODIFIED PYRIMIDINES," issued Nov. 3, 1998 to Froehler et al., U.S. Pat. No. 6,639,059, entitled "SYNTHESIS OF [2.2.1]BICYCLO NUCLEOSIDES," issued Oct. 28, 2003 to Kochkine et al., U.S. Pat. No. 6,303,315, entitled "ONE STEP SAMPLE PREPARATION AND DETECTION OF NUCLEIC ACIDS IN COMPLEX BIOLOGICAL SAMPLES," issued Oct. 16, 2001 to Skouv, and U.S. Pat. Application Pub. No. 2003/0092905, entitled "SYNTHESIS OF [2.2.1]BICYCLO NUCLEOSIDES," by Kochkine et al. that published May 15, 2003, which are each incorporated by reference.

A "nucleotide" refers to an ester of a nucleoside, e.g., a phosphate ester of a nucleoside. To illustrate, a nucleotide can include 1, 2, 3, or more phosphate groups covalently linked to a 5' position of a sugar moiety of the nucleoside.

A "nucleotide incorporating biocatalyst" refers to a catalyst that catalyzes the incorporation of nucleotides into a nucleic acid. Nucleotide incorporating biocatalysts are typically enzymes. An "enzyme" is a protein-and/or nucleic acid-based catalyst that acts to reduce the activation energy of a chemical reaction involving other compounds or "substrates." A "nucleotide incorporating enzyme" refers to an enzyme that catalyzes the incorporation of nucleotides into a nucleic acid, e.g., during nucleic acid amplification or the like. Exemplary nucleotide incorporating enzymes include, e.g., polymerases, terminal transferases, reverse transcriptases, telomerases, polynucleotide phosphorylases, and the like. A "thermostable enzyme" refers to an enzyme that is stable to heat, is heat resistant and retains sufficient catalytic activity when subjected to elevated temperatures for selected periods of time. For example, a thermostable polymerase retains sufficient activity to effect subsequent primer extension reactions when subjected to elevated temperatures for the time necessary to effect denaturation of double-stranded nucleic acids. Heating conditions necessary for nucleic acid denaturation are well known in the art and are exemplified in U.S. Pat. Nos. 4,683,202 and 4,683,195, which are both incorporated by reference. As used herein, a thermostable polymerase is typically suitable for use in a temperature cycling reaction such as the polymerase chain reaction ("PCR"). For a thermostable polymerase, enzymatic activity refers to the catalysis of the combination of the nucleotides in the proper manner to form primer extension products that are complementary to a template nucleic acid (e.g., selected subsequences of an HPV L1 region).

A "nucleotide mismatch" in the context of an oligonucleotide and a corresponding target nucleic acid of the oligonucleotide refers to a nucleotide difference or position of non-complementarity between the oligonucleotide and target nucleic acids when the two nucleic acids are aligned for maximum correspondence. For example, a cross-reactive oligonucleotide of the invention may include one or more nucleotide mismatches with a substantially complementary sequence in the L1 region of a given target high-risk HPV type.

An "oligonucleotide" refers to a nucleic acid that includes at least two nucleic acid monomer units (e.g., nucleotides), typically more than three monomer units, and more typically greater than ten monomer units. The exact size of an oligonucleotide generally depends on various factors, including the ultimate function or use of the oligonucleotide. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (1979) *Meth. Enzymol.* 68:90-99; the phosphodiester method of Brown et al. (1979) *Meth. Enzymol.* 68:109-151; the diethylphosphoramidite method of Beaucage et al. (1981) *Tetrahedron Lett.* 22:1859-1862; the triester method of Matteucci et al. (1981) *J. Am. Chem. Soc.* 103:3185-3191; automated synthesis methods; or the solid support method of U.S. Pat. No. 4,458,066, or other methods known in the art. All of these references are incorporated by reference.

The term "probe nucleic acid" or "probe" refers to a labeled or unlabeled oligonucleotide capable of selectively hybridizing to a target nucleic acid under suitable conditions. Typically, a probe is sufficiently complementary to a specific target sequence (e.g., the L1 region of a high risk HPV type) contained in a nucleic acid sample to form a stable hybridization duplex with the target sequence under a selected hybridization condition, such as, but not limited to, a stringent hybridization condition. A hybridization assay carried out using the probe under sufficiently stringent hybridization conditions permits the selective detection of a specific target sequence. The term "hybridizing region" refers to that region of a nucleic acid that is exactly or substantially complementary to, and therefore hybridizes to, the target sequence. For use in a hybridization assay for the discrimination of single nucleotide differences in sequence, the hybridizing region is typically from about 8 to about 100 nucleotides in length. Although the hybridizing region generally refers to the entire oligonucleotide, the probe may include additional nucleotide sequences that function, for example, as linker binding sites to provide a site for attaching the probe sequence to a solid support or the like. In certain embodiments, a probe of the invention is included in a nucleic acid that comprises one or more labels (e.g., a reporter dye, a quencher moiety, etc.), such as a 5'-nuclease probe, a FRET probe, a molecular beacon, or the like, which can also be utilized to detect hybridization between the probe and target nucleic acids in a sample. In some embodiments, the hybridizing region of the probe is completely complementary to the target sequence. However, in general, complete complementarity is not necessary; stable duplexes may contain mismatched bases or unmatched bases. Modification of the stringent conditions may be necessary to permit a stable hybridization duplex with one or more base pair mismatches or unmatched bases. Sambrook et al., *Molecular Cloning: A Laboratory Manual*, 3rd Ed., Cold Spring Harbor Laboratory Press, Cold Spring Harbor, N.Y. (2001), which is incorporated by reference, provides guidance for suitable modification. Stability of the target/probe duplex depends on a number of variables including length of the oligonucleotide, base composition and sequence of the oligonucleotide, temperature, and ionic conditions. One of skill in the art will recognize that, in general, the exact complement of a given probe is similarly useful as a probe. Exemplary probes of the invention, which bind to the L1 region of a high risk HPV type comprise sequences selected from SEQ ID NOS: 1-31 and complements thereof. One of skill in the art will also recognize that, in certain embodiments, probe nucleic acids can also be used as primer nucleic acids.

A "primer nucleic acid" or "primer" is a nucleic acid that can hybridize to a template nucleic acid (e.g., the L1 region of a high risk HPV type) and permit chain extension or elongation using, e.g., a nucleotide incorporating biocatalyst, such as a polymerase under appropriate reaction conditions. A primer nucleic acid is typically a natural or synthetic oligonucleotide (e.g., a single-stranded oligodeoxyribonucleotide, etc.). Although other primer nucleic acid lengths are optionally utilized, they typically comprise hybridizing regions that range from about 8 to about 100 nucleotides in length. Short primer nucleic acids generally utilize cooler temperatures to form sufficiently stable hybrid complexes with template HPV nucleic acids. A primer nucleic acid that is at least partially complementary to a subsequence of a template HPV nucleic acid is typically sufficient to hybridize with the template for extension to occur. A primer nucleic acid can be labeled, if desired, by incorporating a label detectable by, e.g., spectroscopic, photochemical, biochemical, immunochemical, chemical, or other techniques. To illustrate, useful labels include radioisotopes, fluorescent dyes, electron-dense reagents, enzymes (as commonly used in ELISAs), biotin, or haptens and proteins for which antisera or monoclonal antibodies are available. Many of these and other labels are described further herein and/or otherwise known in the art. Exemplary primer nucleic acids of the invention, which bind to the L1 region of a high risk HPV type comprise sequences selected from SEQ ID NOS: 1-31 and complements thereof. Other suitable primers are also referred to herein and/or known in the art. One of skill in the art will recognize that, in certain embodiments, primer nucleic acids can also be used as probe nucleic acids.

A "quencher moiety" or "quencher" refers to a moiety that reduces and/or is capable of reducing the detectable emission of radiation, e.g., fluorescent or luminescent radiation, from a source that would otherwise have emitted this radiation. A quencher typically reduces the detectable radiation emitted by the source by at least 50%, typically by at least 80%, and more typically by at least 90%. Exemplary quenchers are provided in, e.g., U.S. Pat. No. 6,465,175, entitled "OLIGONUCLEOTIDE PROBES BEARING QUENCHABLE FLUORESCENT LABELS, AND METHODS OF USE THEREOF," which issued Oct. 15, 2002 to Horn et al., which is incorporated by reference.

The term "sample" refers to any substance containing or presumed to contain HPV nucleic acid including, but not limited to, tissue or fluid isolated from one or more subjects or individuals, in vitro cell culture constituents, as well as clinical samples. Exemplary samples include urine, seminal fluid, seminal plasma, prostatic fluid, vaginal fluid, cervical fluid, uterine fluid, cervical scrapings, amniotic fluid, anal scrapings, mucus, sputum, tissue, and the like.

"Selectively hybridizing" or "selective hybridization" in the context of nucleic acid hybridization refers to a nucleic acid that hybridizes or binds to a target HPV nucleic acid (e.g., the L1 region of HPV types 33, 35, 52, and/or 58) to a greater extent than the nucleic acid binds, under the same hybridization conditions, to non-target nucleic acids (e.g., the L1 region of HPV types 6, 11, 26, 40, 42, 43, 44, 53, 54, 55, 57, 64, 66, 67, and 70).

A "set" refers to a collection of at least two molecule or sequence types, e.g., 2, 3, 4, 5, 10, 20, 50, 100, 1,000 or more molecule or sequence types. For example, certain aspects of the invention include reaction mixtures having sets of amplicons. A "subset" refers to any portion of a set.

A "sequence" of a nucleic acid refers to the order and identity of nucleotides in the nucleic acid. A sequence is typically read in the 5' to 3' direction.

A "solid support" refers to a solid material which can be derivatized with, or otherwise attached to, a chemical moiety, such as an oligonucleotide or the like. Exemplary solid supports include plates, microwell plates, beads, microbeads, fibers, whiskers, combs, hybridization chips, membranes, single crystals, ceramic layers, self-assembling monolayers, and the like.

An oligonucleotide is "specific" for a target sequence if the number of mismatches present between the oligonucleotide and the target sequence is less than the number of mismatches present between the oligonucleotide and non-target sequences that might be present in a sample. Hybridization conditions can be chosen under which stable duplexes are formed only if the number of mismatches present is no more than the number of mismatches present between the oligonucleotide and the target sequence. Under such conditions, the target-specific oligonucleotide can form a stable duplex only with a target sequence. Thus, the use of target-specific primers under suitably stringent amplification conditions enables the specific amplification of those sequences which contain the target primer binding sites. Similarly, the use of target-specific oligonucleotides under suitably stringent hybridization conditions enables the detection of a specific target sequence.

A "subsequence" or "segment" refers to any portion of an entire nucleic acid sequence.

A "substantially identical variant" in the context of nucleic acids, refers to two or more sequences that have at least 80%, typically at least 85%, more typically at least 90%, and still more typically at least 95% nucleotide or sequence identity to one another when compared and aligned for maximum correspondence, as measured using, e.g., a sequence comparison algorithm or by visual inspection. In certain embodiments, for example, a substantially identical variant of a nucleic acid includes one or more modified nucleotide substitutions relative to a corresponding unmodified nucleic acid. The substantial identity generally exists over a region of the sequences that is at least about 15 nucleotides in length, more typically over a region that is at least about 20 nucleotides in length, and even more typically the sequences are substantially identical over a region of at least about 25 nucleotides in length. In some embodiments, for example, the sequences are substantially identical over the entire length of the nucleic acids being compared.

The term "substitution" in the context of a nucleic acid sequence refers to an alteration in which at least one nucleotide of the nucleic acid sequence is replaced by a different nucleotide.

The terms "target sequence," "target region," and "target nucleic acid" refer to a region of a nucleic acid which is to be amplified, detected, or otherwise analyzed.

II. Overview

The invention relates to the selective detection of high-risk HPV types, which are types that are commonly considered to be carcinogenic. For example, the cross-reactive oligonucleotides (e.g., probe nucleic acids, primer nucleic acids, etc.) described herein detectably bind, under selected assay conditions, to multiple high-risk HPV types, such as HPV31, HPV33, HPV35, HPV52, HPV56, and/or HPV58. In addition, certain oligonucleotides of the invention have sufficient specificity to exclude the detection of low-risk HPV types, thereby minimizing the occurrence of false positives. Accordingly, high-risk HPV infections can be readily and accurately diagnosed using the methods and reagents described herein. Oligonucleotide specificity is further illustrated, for example, in the example provided below. Many other features of the invention are also described herein.

To further illustrate, certain methods of the invention include acquiring a sample from a patient and amplifying a target nucleic acid from the L1 region of HPV, if HPV is present in the sample. Essentially any nucleic acid amplification technique can be utilized or adapted for use in amplifying the target HPV nucleic acid. In certain embodiments, for example, at least one version of a polymerase chain reaction is used to generate multiple copies of the target nucleic acid. In some embodiments, labeled primer nucleic acids are used in these amplification protocols to facilitate amplicon detection. Target HPV nucleic acids are typically amplified prior to or simultaneously (e.g., for real-time detection) with being contacted with a cross-reactive oligonucleotide of the invention. The oligonucleotide comprises a nucleic acid with a sequence selected from SEQ ID NOS: 1-31, a substantially identical variant thereof, or complements of SEQ ID NOS: 1-31 and the variant. In some embodiments of the invention, bovine serum albumin-conjugated oligonucleotides are attached to the surfaces of microwell plate wells in which the target HPV nucleic acid is amplified. Optionally, the oligonucleotides of the invention are arrayed on other types of solid supports or are present in solution when contacted with the target HPV nucleic acids and/or the amplicons of those targets.

These methods also generally include monitoring (e.g., at a single time point, at multiple discrete time points, continuously over a selected time period, etc.) binding between the amplicons and the cross-reactive oligonucleotides to determine whether HPV is present in the particular samples, e.g., to diagnose patients from which the samples were derived, to monitor courses of treatment for patients diagnosed with HPV infections, and/or the like. In certain embodiments, a detected high-risk HPV is genotyped by determining the temperature (i.e., the $T_m$) at which a target HPV nucleic acid or amplicon thereof dissociates from a given oligonucleotide of the invention upon hybridization. These and many other approaches to detecting and genotyping HPV using the cross-reactive oligonucleotides of the invention are described further herein.

In addition to compositions and reaction mixtures, the invention also relates to kits and systems for detecting and genotyping high-risk HPV, and to related computers and computer readable media.

III. Cross-Reactive Oligonucleotides

The cross-reactive oligonucleotides (e.g., probe nucleic acids, primer nucleic acids, etc.) of the invention bind to the L1 region of, e.g., HPV31, HPV33, HPV35, HPV52, HPV56, and/or HPV58. HPV31 is further described in, e.g., Hubert et al. (1999) "DNA replication of human papillomavirus type 31 is modulated by elements of the upstream regulatory region that lie 5' of the minimal origin," *J. Virol.* 73(3):1835-1845, which is incorporated by reference. HPV33 is also described in, e.g., Cole et al. (1986) "Genome organization and nucleotide sequence of human papillomavirus type 33, which is associated with cervical cancer" *J. Virol.* 58:991-995, which is incorporated by reference. HPV35 is further described in, e.g., Delius et al. (1994) "Primer-directed sequencing of human papillomavirus types" *Curr. Top. Microbiol. Immunol.* 186:13-31, which is incorporated by reference. HPV52 is also described in, e.g., Delius et al. (1994), supra, and Shimoda et al. (1988) "Human papillomavirus type 52: a new virus associated with cervical neoplasia" *J Gen Virol.* 69(11):2925-8, which are both incorporated by reference. HPV56 is also described in, e.g., Delius et al. (1994) "Primer-directed sequencing of human papillomavirus types" *Curr. Top. Microbiol. Immunol.* 186:13-31, which is incorporated by reference. HPV58 is further described in, e.g., Kirii et al. (1991) "Human papillomavirus type 58 DNA sequence" *Virology* 185:424-427, which is incorporated by reference. See also, the HPV Sequence Database provided on the world wide web at hpv-web.lanl.gov as of May 7, 2004.

More specifically, the oligonucleotides of the invention each include a nucleic acid with a sequence selected from SEQ ID NOS: 1-31, a substantially identical variant thereof in which the variant has at least 80% sequence identity to one of SEQ ID NOS: 1-31, and complements of SEQ ID NOS: 1-31 and the variant. SEQ ID NOS: 1-31 are shown in Table I.

TABLE I

| SEQ ID NO | SEQUENCE | DESIGNATION |
|---|---|---|
| 1 | 5'-CAGTACTAAAAGTCATGTTAGTGCT-3' | A5256A |
| 2 | 5'-CAGTACAAATAGTCATGTTAGTGCT-3' | A5256B |
| 3 | 5'-TCATTTTTATATGTGCTTTCCTT-3' | A5258A |
| 4 | 5'-ATTATCATTTTTATATGTACTTTCCTT-3' | A5258B |
| 5 | 5'-TCATTTTTATATGTGCCTTCCTT-3' | A5258C |
| 6 | 5'-TTAAAATTTTCATTTTTATATGTACTTTCCTT-3' | A5258D |
| 7 | 5'-CAGTACATAAAGTCATGTTAGTGCT-3' | A5256C |
| 8 | 5'-TTAAAATTTTCATTTTTATATGT-3' | A3352A |

TABLE I-continued

| SEQ ID NO | SEQUENCE | DESIGNATION |
|---|---|---|
| 9 | 5'-CATAAAGTCATGTTAGTGCTGCGAGT-3' | A3352B |
| 10 | 5'-ATTTTTATATGTGCTTTCCTTTTAATTGCAGCACAAACAGACA-3' | A3152HYB |
| 11 | 5'-AATTGCAGCACAAACAGACAATTTTTATATGTGCTTTCCTTTT-3' | A5231HYB |
| 12 | 5'-TTAAAATTTTCATTTTTATATGTACTTTC-3' | A3X5XA |
| 13 | 5'-AAATTTTCATTTTTATATGTACTTTC-3' | A3X5XB |
| 14 | 5'-TTAAAATTGTCATTTTTATATGTACTTTC-3' | A3X5XE |
| 15 | 5'-TTAAAATPTPCATTTTTATATGPAETTPC-3' | A3X5XC |
| 16 | 5'-TTAAAATZTZCATTTTTATATGZAJTTZC-3' | A3X5XD |
| 17 | 5'-TTAAAAPPTPEAPPPPPAPAPGPAETTPC-3' | A3X5XH |
| 18 | 5'-CATAAAGTCATATTAGTGCTGCGAGTGGTATC-3' | A3352C |
| 19 | 5'-CATAAAGTCAPATTAGTGETGEGAGTGGTATC-3' | A3352D |
| 20 | 5'-TTAAAATPGPCATTTTTATATGPAETTPC-3' | A3X5XF |
| 21 | 5'-TTAAAAPPGPEAPPPPPAPAPGPAETTPC-3' | A3X5XG |
| 22 | 5'-TATTCEPPAAAAPPGPEAPTTTTAPAPGPAEPPPE-3' | A3X5XY5S |
| 23 | 5'-FTATTCQEPPAAAAPPGPEAPTTTTAPAPGPAEPPPEO-3' | FQIA3X5XY5S |
| 24 | 5'-FTATTQCCTTAAAATPTPCATTTTTATATGPAETTPCO-3' | FQIA3X5XA4 |
| 25 | 5'-FTAPPQECPPAAAAPPTPEAPTTTTATAPGPAETTPEO-3' | FQA3X5XA15S |
| 26 | 5'-FTATTQCCTTAAAATPGPCATTTTTATATGPGETGPCO-3' | FQIA3X5XZ4 |
| 27 | 5'-FTAPPQECPPAAAAPPGPEAPTTTTATAPGPGETGPEO-3' | FQA3X5XZ15S |
| 28 | 5'-FTAPPQCCTTAAAATPGPCATTTTTATATGPGETGPCO-3' | FQIA3X5XS4 |
| 29 | 5'-FTATTQCCTTAAAATPGPCATTTTTATATGPAEPTPCO-3' | FQIA3X5XY4 |
| 30 | 5'-FTATTQCEPPAAAAPPGPEATTTTTATAPGPAEPTPCO-3' | FQIA3X5XY12S |
| 31 | 5'-FTATTCQEPPAAAAPPGPEAPTTTTAPAPGPAEPPPEO-3' | FQIA3X5XY5 |

As shown in Table I, P represents 5-propynyl-dU, E represents 5-methyl-dC, Z represents 2'-0-methyl Ribo-U, F represents FAM, Q represents Black Hole Quencher™-2 (BHQ2), O represents phosphate, and J represents 2'-O-methyl Ribo-C. To illustrate, oligonucleotide A3X5XA (SEQ ID NO: 12) has a sequence that has a single mismatch with HPV33 and a single mismatch with HPV52. In addition, oligonucleotide A3X5XA has two mismatches with HPV35 and two mismatches with HPV58. Certain performance characteristics of oligonucleotide A3X5XA and other oligonucleotides are provided below in the example.

The introduction of modified nucleotide substitutions into oligonucleotide sequences can, e.g., increase the melting temperature of the oligonucleotides. In certain embodiments, this can yield greater sensitivity relative to corresponding unmodified oligonucleotides even in the presence of one or more mismatches in sequence between the target nucleic acid and the cross-reactive oligonucleotide. To further illustrate, oligonucleotide A3X5XC (SEQ ID NO: 15) includes five modified nucleotide substitutions (5-propynyl dU and 5-methyl dC). These substitutions are placed near positions of mismatch with the target nucleic acid sequence, e.g., in order to offset the destabilizing effect of a mismatch on the oligonucleotide:target hybrid. Oligonucleotide A3X5XC is also described in the example provided below.

Additional variants of SEQ ID NOS: 1-31, which include other alterations, are also optionally utilized. For example, variants of SEQ ID NOS: 1-31 can include one or more insertions, deletions, or substitutions relative to oligonucleotides that comprise nucleic acids with sequences selected from SEQ ID NOS: 1-31. Other exemplary modified nucleotides that can be substituted in the oligonucleotides of the invention include, e.g., C5-ethyl-dC, C5-methyl-dU, C5-ethyl-dU, 2,6-diaminopurines, C5-propynyl-dC, C7-propynyl-dA, C7-propynyl-dG, C5-propargylamino-dC, C5-propargylamino-dU, C7-propargylamino-dA, C7-propargylamino-dG, 7-deaza-2-deoxyxanthosine, pyrazolopyrimidine analogs, pseudo-dU, nitro pyrrole, nitro indole, 2'-0-methyl Ribo-U, 2'-0-methyl Ribo-C, an 8-aza-dA, an 8-aza-dG, a 7-deaza-dA, a 7-deaza-dG, N4-ethyl-dC, N6-methyl-dA, etc. To further illustrate, other examples of modified oligonucleotides include those having one or more LNA™ monomers. Nucleotide analogs such as these are described further in, e.g., U.S. Pat. No. 6,639,059, entitled "SYNTHESIS OF [2.2.1]BICYCLO NUCLEOSIDES," issued Oct. 28, 2003 to Kochkine et al., U.S. Pat. No. 6,303,315, entitled "ONE STEP SAMPLE PREPARATION AND DETECTION OF NUCLEIC ACIDS IN COMPLEX BIOLOGICAL SAMPLES," issued Oct. 16, 2001 to Skouv, and U.S. Pat.

Application Pub. No. 2003/0092905, entitled "SYNTHESIS OF [2.2.1]BICYCLO NUCLEOSIDES," by Kochkine et al. that published May 15, 2003, which are each incorporated by reference. Oligonucleotides comprising LNA™ monomers are commercially available through, e.g., Exiqon A/S (Vedbæk, DK). Additional oligonucleotide modifications are referred to herein, including in the definitions provided above. It will be appreciated that many of these modifications are also optionally incorporated into primer nucleic acids used in performing the methods of the present invention. Other aspects of the probes and primers utilized as described herein, including synthesis and labeling, are provided below.

Although other lengths are optionally utilized, the oligonucleotides of the invention generally comprise sequences that are typically between about 12 and about 100 nucleotides in length, more typically between about 15 and about 75 nucleotides in length, still more typically between about 20 and about 50 nucleotides in length, and even more typically between about 23 and about 35 nucleotides in length (e.g., about 24, 25, 26, 27, 28, 29, 30, 31, 32, 33, or 34 nucleotides in length). Methods of preparing oligonucleotides, such as nucleic acid synthesis, are described further below.

Various approaches can be utilized by one of skill in the art to design oligonucleotides (e.g., substantially identical variants of nucleic acids having sequences selected from SEQ ID NOS: 1-31 or complements thereof) that selectively hybridize to the L1 region of HPV types 33, 35, 52, and/or 58. To illustrate, the DNAstar software package available from DNASTAR, Inc. (Madison, Wis.) can be used for sequence alignments. For example, nucleic acid sequences from the L1 region of HPV types 33, 35, 52, and/or 58 and non-target sequences can be uploaded into DNAstar EditSeq program as individual files. To further illustrate, pairs of sequence files can be opened in the DNAstar MegAlign sequence alignment program and the Clustal W method of alignment can be applied. The parameters used for Clustal W alignments are optionally the default settings in the software. MegAlign typically does not provide a summary of the percent identity between two sequences. This is generally calculated manually. From the alignments, regions having, e.g., less than 85% identity with one another are typically identified and oligonucleotide sequences in these regions can be selected. Many other sequence alignment algorithms and software packages are also optionally utilized. Sequence alignment algorithms are also described in, e.g., Mount, *Bioinformatics: Sequence and Genome Analysis*, Cold Spring Harbor Laboratory Press (2001), and Durbin et al., *Biological Sequence Analysis: Probabilistic Models of Proteins and Nucleic Acids*, Cambridge University Press (1998), which are both incorporated by reference.

To further illustrate, optimal alignment of sequences for comparison can be conducted, e.g., by the local homology algorithm of Smith & Waterman (1981) *Adv. Appl. Math.* 2:482, by the homology alignment algorithm of Needleman & Wunsch (1970) *J. Mol. Biol.* 48:443, by the search for similarity method of Pearson & Lipman (1988) *Proc. Nat'l. Acad. Sci. USA* 85:2444, which are each incorporated by reference, and by computerized implementations of these algorithms (GAP, BESTFIT, FASTA, and TFASTA in the Wisconsin Genetics Software Package, Genetics Computer Group (Madison, Wis.), or by even by visual inspection.

Another example algorithm that is suitable for determining percent sequence identity is the BLAST algorithm, which is described in, e.g., Altschul et al. (1990) *J. Mol. Biol.* 215:403-410, which is incorporated by reference. Software for performing versions of BLAST analyses is publicly available through the National Center for Biotechnology Information on the world wide web at ncbi.nlm.nih.gov/ as of May 7, 2004. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOS UM62 scoring matrix (see, Henikoff & Henikoff (1989) *Proc. Natl. Acad. Sci. USA* 89:10915, which is incorporated by reference).

In addition to calculating percent sequence identity, the BLAST algorithm also performs a statistical analysis of the similarity between two sequences (see, e.g., Karlin & Altschul (1993) *Proc. Nat'l. Acad. Sci. USA* 90:5873-5787, which is incorporated by reference). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence (and, therefore, homologous) if the smallest sum probability in a comparison of the test nucleic acid to the reference nucleic acid is less than about 0.1, or less than about 0.01, and or even less than about 0.001.

An additional example of a useful sequence alignment algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle (1987) *J. Mol. Evol.* 35:351-360, which is incorporated by reference. The method used is similar to the method described by Higgins & Sharp (1989) *CABIOS* 5:151-153, which is incorporated by reference. The program can align, e.g., up to 300 sequences of a maximum length of 5,000 letters. The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. The final alignment is achieved by a series of progressive, pairwise alignments. The program can also be used to plot a dendogram or tree representation of clustering relationships. The program is run by designating specific sequences and their amino acid or nucleotide coordinates for regions of sequence comparison.

In practicing the present invention, many conventional techniques in molecular biology and recombinant DNA are optionally used. These techniques are well known and are explained in, for example, *Current Protocols in Molecular Biology*, Volumes I, II, and III, 1997 (F. M. Ausubel ed.); Sambrook et al., *Molecular Cloning: A Laboratory Manual*, 3rd Ed., Cold Spring Harbor Laboratory Press, Cold Spring Harbor, N.Y., 2001; Berger and Kimmel, *Guide to Molecular Cloning Techniques, Methods in Enzymology* volume 152 Academic Press, Inc., San Diego, Calif. (Berger), *DNA Cloning: A Practical Approach*, Volumes I and II, 1985 (D. N. Glover ed.); *Oligonucleotide Synthesis*, 1984 (M. L. Gait ed.); *Nucleic Acid Hybridization*, 1985, (Hames and Higgins); *Transcription and Translation*, 1984 (Hames and Higgins eds.); *Animal Cell Culture*, 1986 (Freshney ed.); *Immobilized Cells and Enzymes*, 1986 (IRL Press); Perbal, 1984, *A Practical Guide to Molecular Cloning*; the series, *Methods in Enzymology* (Academic Press, Inc.); *Gene Transfer Vectors for Mammalian Cells*, 1987 (J. H. Miller and M. P. Calos eds., Cold Spring Harbor Laboratory); *Methods in Enzymology* Vol. 154 and Vol. 155 (Wu and Grossman, and Wu, eds., respectively), all of which are incorporated by reference.

IV. Sequence Variations

Numerous nucleic acid and polypeptide sequences are within the scope of the present invention, whether as target sequences or the agents used to detect those target sequences.

Silent Variations

It will be appreciated by those skilled in the art that due to the degeneracy of the genetic code, a multitude of nucleic acids sequences from the L1 open reading frame of high-risk HPV types (e.g., HPV31, HPV33, HPV35, HPV52, HPV56, and/or HPV58) may be produced, some of which may bear minimal sequence homology to the nucleic acid sequences explicitly disclosed herein. For instance, inspection of the codon table (Table II) shows that codons AGA, AGG, CGA, CGC, CGG, and CGU all encode the amino acid arginine. Thus, at every position in the nucleic acids of the invention where an arginine is specified by a codon, the codon can be altered to any of the corresponding codons described above without altering an encoded polypeptide. It is understood that U in an RNA sequence corresponds to T in a DNA sequence.

TABLE II

Codon Table

| Amino acids | | | Codon | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |

TABLE II-continued

Codon Table

| Amino acids | | | Codon | | | | | |
|---|---|---|---|---|---|---|---|---|
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

Such "silent variations" are one species of "conservatively modified variations", discussed below. One of skill will recognize that each codon in a nucleic acid (except AUG, which is ordinarily the only codon for methionine) can be modified by standard techniques to encode a functionally identical polypeptide. Accordingly, each silent variation of a nucleic acid, which encodes a polypeptide is implicit in any described sequence. The invention provides each and every possible variation of nucleic acid sequence of the L1 open reading frame of HPV31, HPV33, HPV35, HPV52, HPV56, and HPV58 that could be made by selecting combinations based on possible codon choices. These combinations are made in accordance with the standard triplet genetic code (e.g., as set forth in Table II) as applied to the nucleic acid sequences of these open reading frames. All such variations of every nucleic acid herein are specifically provided and described by consideration of the sequence in combination with the genetic code.

Conservative Variations

"Conservatively modified variations" or, simply, "conservative variations" of a particular nucleic acid sequence refers to those nucleic acids, which encode identical or essentially identical amino acid sequences, or, where the nucleic acid does not encode an amino acid sequence, to essentially identical sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid.

Conservative substitution tables providing functionally similar amino acids are well known in the art. Table III sets forth six groups, which contain amino acids that are "conservative substitutions" for one another.

TABLE III

Conservative Substitution Groups

| | | | |
|---|---|---|---|
| 1 | Alanine (A) | Serine (S) | Threonine (T) |
| 2 | Aspartic acid (D) | Glutamic acid (E) | |
| 3 | Asparagine (N) | Glutamine (Q) | |
| 4 | Arginine (R) | Lysine (K) | |

TABLE III-continued

Conservative Substitution Groups

| | | | |
|---|---|---|---|
| 5 Isoleucine (I) | Leucine (L) | Methionine (M) | Valine (V) |
| 6 Phenylalanine (F) | Tyrosine (Y) | Tryptophan (W) | |

Thus, "conservatively substituted variations" of a polypeptide encoded by the L1 open reading frame of HPV31, HPV33, HPV35, HPV52, HPV 56, and HPV58 referred to herein include substitutions of a small percentage, typically less than 5%, more typically less than 2% or 1%, of the amino acids of the polypeptide sequence, with a conservatively selected amino acid of the same conservative substitution group.

The addition of sequences that do not alter the encoded activity of a nucleic acid molecule, such as the addition of a non-functional sequence, is a conservative variation of the basic nucleic acid.

One of skill will appreciate that many conservative variations of the nucleic acids described herein yield a functionally identical nucleic acid. For example, as discussed above, owing to the degeneracy of the genetic code, "silent substitutions" (i.e., substitutions in a nucleic acid sequence which do not result in an alteration in an encoded polypeptide) are an implied feature of every nucleic acid sequence, which encodes an amino acid. Similarly, "conservative amino acid substitutions," in one or a few amino acids in an amino acid sequence are substituted with different amino acids with highly similar properties, are also readily identified as being highly similar to a disclosed construct. Such conservative variations of each disclosed sequence are a feature of the present invention.

V. Probe and Primer Preparation

Many different primer pairs are optionally used to amplify target HPV DNA.

Examples of suitable primer pairs directed to conserved regions among different HPV types in the L1 region include MY11/MY09 and GP5/GP6. These primers are also described in, e.g., Manos et al. (1989) "The use of polymerase chain reaction amplification for the detection of genital human papillomaviruses" *Cancer Cells* 7:209-214, and Van den Brule et al. (1990) "General primer-mediated polymerase chain reaction permits the detection of sequenced and still unsequenced human papillomavirus genotypes in cervical scrapes and carcinomas" *Int. J. Cancer* 45:644-649, which are both incorporated by reference. These and other primer pairs are also described in, e.g., U.S. Pat. Nos. 6,482,588 and 5,705,627, U.S. Pat. Application Pub. No. US 2003/0059806 A1, and European Pat. Application Pub. No. EP 1302550 A1, which are each incorporated by reference.

The oligonucleotide probes and primers of the invention are optionally prepared using essentially any technique known in the art. In certain embodiments, for example, the oligonucleotide probes and primers described herein are synthesized chemically using essentially any nucleic acid synthesis method, including, e.g., according to the solid phase phosphoramidite method described by Beaucage and Caruthers (1981), *Tetrahedron Letts.* 22(20):1859-1862, which is incorporated by reference. To further illustrate, oligonucleotides can also be synthesized using a triester method (see, e.g., Capaldi et al. (2000) "Highly efficient solid phase synthesis of oligonucleotide analogs containing phosphorodithioate linkages" *Nucleic Acids Res.* 28(9):e40 and Eldrup et al. (1994) "Preparation of oligodeoxyribonucleoside phosphorodithioates by a triester method" *Nucleic Acids Res.* 22(10):1797-1804, which are both incorporated by reference). Other synthesis techniques known in the art can also be utilized, including, e.g., using an automated synthesizer, as described in Needham-VanDevanter et al. (1984) *Nucleic Acids Res.* 12:6159-6168, which is incorporated by reference. A wide variety of equipment is commercially available for automated oligonucleotide synthesis. Multi-nucleotide synthesis approaches (e.g., tri-nucleotide synthesis, etc.) are also optionally utilized. Moreover, the primer nucleic acids described herein optionally include various modifications. In certain embodiments, for example, primers include restriction site linkers, e.g., to facilitate subsequent amplicon cloning or the like. To further illustrate, primers are also optionally modified to improve the specificity of amplification reactions as described in, e.g., U.S. Pat. No. 6,001,611, entitled "MODIFIED NUCLEIC ACID AMPLIFICATION PRIMERS," issued Dec. 14, 1999 to Will, which is incorporated by reference. Primers and probes can also be synthesized with various other modifications as described herein or as otherwise known in the art.

Essentially any label is optionally utilized to label the probes and/or primers described herein. In some embodiments, for example, the label comprises a fluorescent dye (e.g., a rhodamine dye (e.g., R6G, R110, TAMRA, ROX, etc.), a fluorescein dye (e.g., JOE, VIC, TET, HEX, FAM, etc.), a halofluorescein dye, a cyanine dye (e.g., CY3, CY3.5, CY5, CY5.5, etc.), a BODIPY® dye (e.g., FL, 530/550, TR, TMR, etc.), an ALEXA FLUOR® dye (e.g., 488, 532, 546, 568, 594, 555, 653, 647, 660, 680, etc.), a dichlororhodamine dye, an energy transfer dye (e.g., BIGDYE™ v 1 dyes, BIGDYE™ v 2 dyes, BIGDYE™ v 3 dyes, etc.), Lucifer dyes (e.g., Lucifer yellow, etc.), CASCADE BLUE®, Oregon Green, and the like. Additional examples of fluorescent dyes are provided in, e.g., Haugland, *Molecular Probes Handbook of Fluorescent Probes and Research Products*, Ninth Ed. (2003) and the updates thereto, which are each incorporated by reference. Fluorescent dyes are generally readily available from various commercial suppliers including, e.g., Molecular Probes, Inc. (Eugene, Oreg.), Amersham Biosciences Corp. (Piscataway, N.J.), Applied Biosystems (Foster City, Calif.), etc. Other labels include, e.g., biotin, weakly fluorescent labels (Yin et al. (2003) *Appl Environ Microbiol.* 69(7):3938, Babendure et al. (2003) *Anal. Biochem.* 317(1):1, and Jankowiak et al. (2003) *Chem Res Toxicol.* 16(3):304), non-fluorescent labels, colorimetric labels, chemiluminescent labels (Wilson et al. (2003) *Analyst.* 128(5):480 and Roda et al. (2003) *Luminescence* 18(2):72), Raman labels, electrochemical labels, bioluminescent labels (Kitayama et al. (2003) *Photochem Photobiol.* 77(3):333, Arakawa et al. (2003) *Anal. Biochem.* 314(2):206, and Maeda (2003) *J. Pharm. Biomed. Anal.* 30(6):1725), and an alpha-methyl-PEG labeling reagent as described in, e.g., U.S. Provisional Patent Application No. 60/428,484, filed on Nov. 22, 2002, which references are each incorporated by reference. Nucleic acid labeling is also described further below.

In addition, essentially any nucleic acid (and virtually any labeled nucleic acid, whether standard or non-standard) can be custom or standard ordered from any of a variety of commercial sources, such as The Midland Certified Reagent Company, The Great American Gene Company, ExpressGen Inc., Operon Technologies Inc., Proligo LLC, and many others.

VI. Sample Preparation and Nucleic Acid Amplification

Samples are generally derived or isolated from subjects, typically mammalian subjects, more typically human subjects, e.g., suspected of having HPV infections or as part of screening examinations. Exemplary samples or specimens include urine, seminal fluid, seminal plasma, prostatic fluid, vaginal fluid, cervical fluid, uterine fluid, cervical scrapings, amniotic fluid, anal scrapings, mucus, sputum, tissue, and the like. Essentially any technique for acquiring these samples is optionally utilized including, e.g., scraping, venipuncture, swabbing (e.g., using a cervical swab or brush), biopsy, or other techniques known in the art. Methods of storing specimens, culturing cells, extracting or otherwise isolating and preparing nucleic acids from these sources are generally known in the art and many of these are described further in the references provided herein. For example, one of the most powerful and basic technologies for deriving and detecting nucleic acids is nucleic acid amplification. In the present invention, amplification of nucleic acids of interest typically precedes or is concurrent with the detection of that DNA. In addition, the oligonucleotides described herein are also optionally amplified, e.g., following chemical synthesis or the like. In some embodiments, detectable signals are amplified, e.g., using branched nucleic acid or other signal amplification formats known in the art.

Amplification methods that are optionally utilized include, e.g., various polymerase or ligase mediated amplification methods, such as the polymerase chain reaction (PCR), the ligase chain reaction (LCR), and/or the like. Details regarding the use of these and other amplification methods can be found in any of a variety of standard texts, including, e.g., Berger, Sambrook, Ausubel, and *PCR Protocols A Guide to Methods and Applications* (Innis et al. eds) Academic Press, Inc., San Diego, Calif. (1990) (Innis), all of which are incorporated by reference. Many available biology texts also have extended discussions regarding PCR and related amplification methods. Nucleic acid amplification is also described in, e.g., Mullis et al., (1987) U.S. Pat. No. 4,683,202 and Sooknanan (1995) *Biotechnology* 13:563, which are both incorporated by reference. Improved methods of amplifying large nucleic acids by PCR are summarized in Cheng et al. (1994) *Nature* 369:684, which is incorporated by reference. In certain embodiments, duplex PCR is utilized to amplify target nucleic acids. Duplex PCR amplification is described further in, e.g., Gabriel et al. (2003) "Identification of human remains by immobilized sequence-specific oligonucleotide probe analysis of mtDNA hypervariable regions I and II," *Croat. Med. J.* 44(3)293 and La et al. (2003) "Development of a duplex PCR assay for detection of *Brachyspira hyodysenteriae* and *Brachyspira pilosicoli* in pig feces," *J. Clin. Microbiol.* 41(7):3372, which are both incorporated by reference. Optionally, labeled primers (e.g., biotinylated primers, etc.) are utilized to amplify nucleic acids in a sample, e.g., to facilitate detection of hybridization between amplicons and the oligonucleotides of the invention. Labeling is described further herein.

Amplicons are optionally recovered and purified from other reaction components by any of a number of methods well known in the art, including electrophoresis, chromatography, precipitation, dialysis, filtration, and/or centrifugation. Aspects of nucleic acid purification are described in, e.g., Douglas et al., *DNA Chromatography*, Wiley, John & Sons, Inc. (2002), and Schott, *Affinity Chromatography: Template Chromatography of Nucleic Acids and Proteins*, Chromatographic Science Series, #27, Marcel Dekker (1984), all of which are incorporated by reference. In certain embodiments, amplicons are not purified prior to detection. The detection of amplicons is described further below.

VII. Oligonucleotide Arrays

In certain embodiments of the invention, the oligonucleotides described herein are covalently or noncovalently attached to solid supports which are then contacted with samples comprising amplified and labeled nucleic acid from a subject. In other embodiments, the oligonucleotides of the invention are provided free in solution. Essentially any substrate material is optionally adapted for use in these aspects of the invention. In certain embodiments, for example, substrates are fabricated from silicon, glass, or polymeric materials (e.g., glass or polymeric microscope slides, silicon wafers, etc.). Suitable glass or polymeric substrates, including microscope slides, are available from various commercial suppliers, such as Fisher Scientific (Pittsburgh, Pa.) or the like. In some embodiments, solid supports utilized in the invention are membranes. Suitable membrane materials are optionally selected from, e.g. polyaramide membranes, polycarbonate membranes, porous plastic matrix membranes (e.g., POREX® Porous Plastic, etc.), porous metal matrix membranes, polyethylene membranes, poly(vinylidene difluoride) membranes, polyamide membranes, nylon membranes, ceramic membranes, polyester membranes, polytetrafluoroethylene (TEFLON®) membranes, woven mesh membranes, microfiltration membranes, nanofiltration membranes, ultrafiltration membranes, dialysis membranes, composite membranes, hydrophilic membranes, hydrophobic membranes, polymer-based membranes, a non-polymer-based membranes, powdered activated carbon membranes, polypropylene membranes, glass fiber membranes, glass membranes, nitrocellulose membranes, cellulose membranes, cellulose nitrate membranes, cellulose acetate membranes, polysulfone membranes, polyethersulfone membranes, polyolefin membranes, or the like. Many of these membranous materials are widely available from various commercial suppliers, such as, P. J. Cobert Associates, Inc. (St. Louis, Mo.), Millipore Corporation (Bedford, Mass.), or the like. Other exemplary solid supports that are optionally utilized include, e.g., ceramics, metals, resins, gels, plates, microwell plates, beads, microbeads, whiskers, fibers, combs, single crystals, and self-assembling monolayers.

The oligonucleotides of the invention are directly or indirectly (e.g., via linkers, such as bovine serum albumin (BSA) or the like) attached to the supports, e.g., by any available chemical or physical method. A wide variety of linking chemistries are available for linking molecules to a wide variety of solid supports. More specifically, nucleic acids may be attached to the solid support by covalent binding such as by conjugation with a coupling agent or by non-covalent binding such as electrostatic interactions, hydrogen bonds or antibody-antigen coupling, or by combinations thereof. Typical coupling agents include biotin/avidin, biotin/streptavidin, *Staphylococcus aureus* protein A/IgG antibody $F_c$ fragment, and streptavidin/protein A chimeras (Sano et al. (1991) *Bio/Technology* 9:1378, which is incorporated by reference), or derivatives or combinations of these agents. Nucleic acids may be attached to the solid support by a photocleavable bond, an electrostatic bond, a disulfide bond, a peptide bond, a diester bond or a combination of these bonds. Nucleic acids are also optionally attached to solid supports by a selectively releasable bond such as 4,4'-dimethoxytrityl or its derivative. Derivatives which have been found to be useful include 3 or 4 [bis-(4-methoxyphenyl)]-methyl-benzoic acid, N-succinimidyl-3 or 4 [bis-(4-methoxyphenyl)]-methyl-benzoic acid, N-succinimidyl-3 or 4 [bis-(4-methoxyphenyl)]-hydroxymethyl-benzoic acid, N-succinimidyl-3 or 4 [bis-(4-methoxyphenyl)]-chloromethyl-benzoic acid, and salts of these acids.

As referred to above, oligonucleotides are optionally attached to solid supports via linkers between the nucleic acids and the solid support. Useful linkers include a coupling agent, as described above for binding to other or additional coupling partners, or to render the attachment to the solid support cleavable.

Cleavable attachments can be created by attaching cleavable chemical moieties between the oligonucleotides and the solid support including, e.g., an oligopeptide, oligonucleotide, oligopolyamide, oligoacrylamide, oligoethylene glycerol, alkyl chains of between about 6 to 20 carbon atoms, and combinations thereof. These moieties may be cleaved with, e.g., added chemical agents, electromagnetic radiation, or enzymes. Exemplary attachments cleavable by enzymes include peptide bonds which can be cleaved by proteases, and phosphodiester bonds which can be cleaved by nucleases.

Chemical agents such as β-mercaptoethanol, dithiothreitol (DTT) and other reducing agents cleave disulfide bonds. Other agents which may be useful include oxidizing agents, hydrating agents and other selectively active compounds. Electromagnetic radiation such as ultraviolet, infrared and visible light cleave photocleavable bonds. Attachments may also be reversible, e.g., using heat or enzymatic treatment, or reversible chemical or magnetic attachments. Release and reattachment can be performed using, e.g., magnetic or electrical fields.

Array based hybridization is particularly suitable for detecting HPV nucleic acids, as it can be used to detect the presence of many amplicons simultaneously. A number of array systems have been described and can be adapted for use with the present invention. Aspects of array construction and use are also described in, e.g., Sapolsky et al. (1999) "High-throughput polymorphism screening and genotyping with high-density oligonucleotide arrays." *Genetic Analysis Biomolecular Engineering* 14:187-192; Lockhart (1998) "Mutant yeast on drugs" *Nature Medicine* 4:1235-1236; Fodor (1997) "Genes, Chips and the Human Genome." *FASEB Journal* 11:A879; Fodor (1997) "Massively Parallel Genomics" *Science* 277: 393-395; and Chee et al. (1996) "Accessing Genetic Information with High-Density DNA Arrays" *Science* 274:610-614, all of which are incorporated by reference.

Other probes and primers for detecting HPV nucleic acids, which are optionally utilized in addition to the probes and primer described above to perform the methods and other aspects of the invention, are described in, e.g., U.S. Pat. No. 5,705,627 to Manos et al., which is incorporated by reference.

VIII. Nucleic acid Hybridization

Hybridization of oligonucleotides to their target HPV nucleic acids can be accomplished by choosing the appropriate hybridization conditions. The stability of the oligonucleotide:target nucleic acid hybrid is typically selected to be compatible with the assay and washing conditions so that stable, detectable hybrids form only between the oligonucleotides and target HPV nucleic acids. Manipulation of one or more of the different assay parameters determines the exact sensitivity and specificity of a particular hybridization assay.

More specifically, hybridization between complementary bases of DNA, RNA, PNA, or combinations of DNA, RNA and PNA, occurs under a wide variety of conditions that vary in temperature, salt concentration, electrostatic strength, buffer composition, and the like. Examples of these conditions and methods for applying them are described in, e.g., Tijssen (1993), supra, and Hames and Higgins, supra. Hybridization generally takes place between about 0° C. and about 70° C., for periods of from about one minute to about one hour, depending on the nature of the sequence to be hybridized and its length. However, it is recognized that hybridizations can occur in seconds or hours, depending on the conditions of the reaction. To illustrate, typical hybridization conditions for a mixture of two 20-mers is to bring the mixture to 68° C., followed by cooling to room temperature (22° C.) for five minutes or at very low temperatures such as 2° C. in 2 microliters. Hybridization between nucleic acids may be facilitated using buffers such as Tris-EDTA (TE), Tris-HCl and HEPES, salt solutions (e.g. NaCl, KCl, $CaCl_2$), or other aqueous solutions, reagents and chemicals. Examples of these reagents include single-stranded binding proteins such as Rec A protein, T4 gene 32 protein, *E. coli* single-stranded binding protein and major or minor nucleic acid groove binding proteins. Other examples of such reagents and chemicals include divalent ions, polyvalent ions and intercalating substances such as ethidium bromide, actinomycin D, psoralen, and angelicin. An exemplary hybridization procedure of use in the present invention follows similar conditions as specified in the AMPLICOR® HPV Test protocol (Roche Diagnostics Corporation, Indianapolis, Ind.).

IX. Detection and Oligonucleotide Variations

As referred to above, amplified target HPV nucleic acid in the samples utilized in the methods of the invention is optionally labeled to permit detection of oligonucleotide-target hybridization duplexes. In general, a label can be any moiety which can be attached, e.g., to a primer utilized for amplification and provide a detectable signal (e.g., a quantifiable signal). Labels may be attached to a primer directly or indirectly by a variety of techniques known in the art. Depending on the type of label used, the label can be attached to a terminal (5' or 3' end of the primer) or a non-terminal nucleotide, and can be attached indirectly through linkers or spacer arms of various sizes and compositions. Using commercially available phosphoramidite reagents, one can produce oligomers containing functional groups (e.g., thiols or primary amines) at either the 5' or 3' terminus via an appropriately protected phosphoramidite, and can label such oligonucleotides using protocols described in, for example, *PCR Protocols: A Guide to Methods and Applications* (Innis et al, eds. Academic Press, Inc. (1990)), which is incorporated by reference. In one embodiment, the label consists of a biotin molecule covalently bound to the primer at the 5' end. The term "biotinylated primer" refers to a primer with one or more biotin molecules bound either directly to the primer or indirectly through intervening linker molecules.

To further illustrate, detection of oligonucleotide-target hybridization duplexes is optionally by a chemiluminescent assay using a luminol-based reagent as described in, e.g., Whitehead, et al. (1983) *Nature* 30(5):158, which is incorporated by reference, and available commercially. Following hybridization of the oligonucleotide with the labeled target DNA, the biotin molecule attached to the target DNA is conjugated, e.g., to streptavidin-horseradish peroxidase (SA-HRP). Alternatively, the target DNA can be labeled with horseradish peroxidase directly, thereby eliminating the separate conjugation step. In either case, subsequent oxidation of luminol by the horseradish peroxidase enzyme results in the emission of photons, which is then detected, e.g., on standard autoradiography film. The intensity of the signal is a function of DNA quantity. A series of DNA standards containing known amounts of DNA are typically assayed along with one or more unknown samples. The signal intensities of the known DNA standards allows an empirical determination of the functional relationship between signal intensity and DNA quantity, which enables the quantitation of the unknown samples. Many other methods of detection are also optionally utilized to perform the methods of the invention and are referred to in the references cited herein and/or generally known in the art.

Any available method for detecting HPV amplicons can be used in the present invention. Common approaches include real time amplification detection with molecular beacons or 5'-nuclease probes, detection of intercalating dyes, detection of labels incorporated into the amplification probes or the amplified nucleic acids themselves (e.g., following electrophoretic separation of the amplification products from unincorporated label), hybridization based assays (e.g., array based assays) and/or detection of secondary reagents that bind to the nucleic acids. For example, a molecular beacon or a 5'-nuclease probe is optionally designed to include an oligonucleotide of the invention (i.e., is selected from SEQ ID NOS: 1-31) or complements thereto), which molecular beacon or 5'-nuclease probe can be used to detect HPV amplicons. Molecular beacons or 5'-nuclease probes are described further below. Details on these general approaches are found in the references cited herein, e.g., Sambrook and Ausubel. Additional strategies for labeling nucleic acids and corresponding detection strategies can be found, e.g., in Haugland (2003) *Handbook of Fluorescent Probes and Research Chemicals Ninth Edition* by Molecular Probes, Inc. (Eugene, Oreg.), which is incorporated by reference.

Molecular beacons (MBs) are oligonucleotides designed for real time detection and quantification of target nucleic acids (e.g., target HPV amplicons). The 5' and 3' termini of MBs collectively comprise a pair of moieties which confers the detectable properties of the MB. One of the termini is attached to a fluorophore and the other is attached to a quencher molecule capable of quenching a fluorescent emission of the fluorophore. For example, one example fluorophore-quencher pair can use a fluorophore such as EDANS or fluorescein, e.g., on the 5'-end and a quencher such as Dabcyl, e.g., on the 3'-end. When the MB is present free in solution, i.e., not hybridized to a second nucleic acid, the stem of the MB is stabilized by complementary base pairing. This self-complementary pairing results in a "hairpin loop" structure for the MB in which the fluorophore and the quenching moieties are proximal to one another. In this confirmation, the fluorescent moiety is quenched by the fluorophore. The loop of the molecular beacon typically comprises an oligonucleotide described herein (e.g., an oligonucleotide selected from SEQ ID NOS: 1-31 or complements thereto) and is accordingly complementary to a sequence to be detected in the target HPV nucleic acid, such that hybridization of the loop to its complementary sequence in the target forces disassociation of the stem, thereby distancing the fluorophore and quencher from each other. This results in unquenching of the fluorophore, causing an increase in fluorescence of the MB.

Details regarding standard methods of making and using MBs are well established in the literature and MBs are available from a number of commercial reagent sources. Further details regarding methods of MB manufacture and use are found, e.g., in Leone et al. (1995) "Molecular beacon probes combined with amplification by NASBA enable homogenous real-time detection of RNA," *Nucleic Acids Res.* 26:2150-2155; Hsuih et al. (1997) "Novel, ligation-dependent PCR assay for detection of hepatitis C in serum" *J Clin Microbiol* 34:501-507; Kostrikis et al. (1998) "Molecular beacons: spectral genotyping of human alleles" *Science* 279:1228-1229; Sokol et al. (1998) "Real time detection of DNA:RNA hybridization in living cells" *Proc. Natl. Acad. Sci. U.S.A.* 95:11538-11543; Tyagi et al. (1998) "Multicolor molecular beacons for allele discrimination" *Nature Biotechnology* 16:49-53; Fang et al. (1999) "Designing a novel molecular beacon for surface-immobilized DNA hybridization studies" *J. Am. Chem. Soc.* 121:2921-2922; and Marras et al. (1999) "Multiplex detection of single-nucleotide variation using molecular beacons" *Genet. Anal. Biomol. Eng.* 14:151-156, all of which are incorporated by reference. Aspects of MB construction and use are also found in patent literature, such as U.S. Pat. No. 5,925,517 (Jul. 20, 1999) to Tyagi et al. entitled "Detectably labeled dual conformation oligonucleotide probes, assays and kits;" U.S. Pat. No. 6,150,097 to Tyagi et al (Nov. 21, 2000) entitled "Nucleic acid detection probes having non-FRET fluorescence quenching and kits and assays including such probes" and U.S. Pat. No. 6,037,130 to Tyagi et al (Mar. 14, 2000), entitled "Wavelength-shifting probes and primers and their use in assays and kits," all of which are incorporated by reference.

MB components (e.g., oligos, including those labeled with fluorophores or quenchers) can be synthesized using conventional methods. Some of these methods are described further above. For example, oligonucleotides or peptide nucleic acids (PNAs) can be synthesized on commercially available automated oligonucleotide/PNA synthesis machines using standard methods. Labels can be attached to the oligonucleotides or PNAs either during automated synthesis or by post-synthetic reactions which have been described before see, e.g., Tyagi and Kramer (1996), supra. Aspects relating to the synthesis of functionalized oligonucleotides can also be found in Nelson, et al. (1989) "Bifunctional Oligonucleotide Probes Synthesized Using A Novel CPG Support Are Able To Detect Single Base Pair Mutations" *Nucleic Acids Res.* 17:7187-7194, which is incorporated by reference. Labels/quenchers can be introduced to the oligonucleotides or PNAs, e.g., by using a controlled-pore glass column to introduce, e.g., the quencher (e.g., a 4-dimethylaminoazobenzene-4'-sulfonyl moiety (DABSYL). For example, the quencher can be added at the 3' end of oligonucleotides during automated synthesis; a succinimidyl ester of 4-(4'-dimethylaminophenylazo)benzoic acid (DABCYL) can be used when the site of attachment is a primary amino group; and 4-dimethylaminophenylazophenyl-4'-maleimide (DABMI) can be used when the site of attachment is a sulphydryl group. Similarly, fluorescein can be introduced in the oligonucleotides, either using a fluorescein phosphoramadite that replaces a nucleoside with fluorescein; or by using a fluorescein dT phosphoramadite that introduces a fluorescein moiety at a thymidine ring via a linker. To link a fluorescein moiety to a terminal location, iodoacetoamidofluorescein can be coupled to a sulphydryl group. Tetrachlorofluorescein (TET) can be introduced during automated synthesis using a 5'-tetrachloro-fluorescein phosphoramadite. Other reactive fluorophore derivatives and their respective sites of attachment include the succinimidyl ester of 5-carboxyrhodamine-6G (RHD) coupled to an amino group; an iodoacetamide of tetramethylrhodamine coupled to a sulphydryl group; an isothiocyanate of tetramethylrhodamine coupled to an amino group; or a sulfonylchloride of Texas red coupled to a sulphydryl group. During the synthesis of these labeled components, conjugated oligonucleotides or PNAs can be purified, if desired, e.g., by high pressure liquid chromatography or other methods.

A variety of commercial suppliers produce standard and custom molecular beacons, including Cruachem (cruachem.com), Oswel Research Products Ltd. (UK; oswel.com), Research Genetics (a division of Invitrogen, Huntsville Ala. (resgen.com)), the Midland Certified Reagent Company (Midland, Tex. mcrc.com) and Gorilla Genomics, LLC (Alameda, Calif.). A variety of kits which utilize molecular beacons are also commercially available, such as the Sentinel™ Molecular Beacon Allelic Discrimination Kits from Stratagene (La Jolla, Calif.) and various kits from Eurogentec SA (Belgium, eurogentec.com) and Isogen Bioscience BV (The Netherlands, isogen.com).

In one embodiment, a real time PCR assay system that includes one or more 5'-nuclease probes is used for detecting amplified HPV nucleic acids. These systems operate by using the endogenous endonuclease activity of certain polymerases to cleave a quencher or label free from an oligonucleotide of the invention that comprises the quencher and label, resulting in unquenching of the label. The polymerase only cleaves the quencher or label upon initiation of replication, i.e., when the oligonucleotide is bound to the template and the polymerase extends the primer. Thus, an appropriately labeled oligonucleotide probe and polymerase comprising the appropriate nuclease activity can be used to detect an HPV nucleic acid of interest. Real time PCR product analysis by, e.g., Fluorescent Resonance Energy Transfer (FRET) or the like provides a well-known technique for real time PCR monitoring that has been used in a variety of contexts, which can be adapted for use with the oligonucleotides and methods described herein (see, Laurendeau et al. (1999) "TaqMan PCR-based gene dosage assay for predictive testing in individuals from a cancer family with INK4 locus haploinsufficiency" *Clin Chem* 45(7):982-6; Laurendeau et al. (1999) "Quantitation of MYC gene expression in sporadic breast tumors with a real-time reverse transcription-PCR assay" *Clin Chem* 59(12):2759-65; and Kreuzer et al. (1999) "LightCycler technology for the quantitation of bcr/abl fusion transcripts" *Cancer Research* 59(13):3171-4, all of which are incorporated by reference).

X. Systems

The invention also provides a system for detecting HPV in a sample. The system includes one or more oligonucleotides as described herein. In certain embodiments, the oligonucleotides are arrayed on a solid support, whereas in others, they are provided in one or more containers, e.g., for assays performed in solution. The system also includes at least one detector (e.g., a spectrometer, etc.) that detects binding between nucleic acids and/or amplicons thereof from the sample and the oligonucleotides. Other detectors are described further below. In addition, the system also includes at least one controller operably connected to the detector. The controller includes one or more instructions sets that correlate the binding detected by the detector with a presence of HPV in the sample.

As referred to above, at least one container or solid support includes the oligonucleotides in some embodiments of the invention. In these embodiments, the system optionally further includes at least one thermal modulator operably connected to the container or solid support to modulate temperature in the container or on the solid support, and/or at least one fluid transfer component (e.g., an automated pipettor, etc.) that transfers fluid to and/or from the container or solid support, e.g., for performing one or more nucleic acid amplification techniques and/or nucleic acid hybridization assays in the container or on the solid support.

Exemplary commercially available systems that are optionally utilized to detect HPV nucleic acids using the oligonucleotides described herein include, e.g., a COBAS TaqMan™ Analyzer or a COBAS AMPLICOR® Analyzer which are available from Roche Diagnostics Corporation (Indianapolis, Ind.), a LUMINEX 100™ system, which is available from the Luminex Corporation (Austin, Tex.), and the like.

The invention further provides a system that includes a computer or computer readable medium that includes a data set that comprises at least one character string that corresponds to at least one sequence selected from the group consisting of: SEQ ID NOS: 1-31 and complements thereof. Typically, the system further includes an automatic synthesizer coupled to an output of the computer or computer readable medium. The automatic synthesizer accepts instructions from the computer or computer readable medium, which instructions direct synthesis of, e.g., one or more nucleic acids that correspond to one or more character strings in the data set. Exemplary systems and system components are described further below.

Detectors are structured to detect detectable signals produced, e.g., in or proximal to another component of the system (e.g., in container, on a solid support, etc.). Suitable signal detectors that are optionally utilized, or adapted for use, in these systems detect, e.g., fluorescence, phosphorescence, radioactivity, absorbance, refractive index, luminescence, or the like. Detectors optionally monitor one or a plurality of signals from upstream and/or downstream of the performance of, e.g., a given assay step. For example, the detector optionally monitors a plurality of optical signals, which correspond in position to "real time" results. Example detectors or sensors include photomultiplier tubes, CCD arrays, optical sensors, temperature sensors, pressure sensors, pH sensors, conductivity sensors, scanning detectors, or the like. Each of these as well as other types of sensors is optionally readily incorporated into the systems described herein. Optionally, the systems of the present invention include multiple detectors.

More specific exemplary detectors that are optionally utilized in these systems include, e.g., a resonance light scattering detector, an emission spectroscope, a fluorescence spectroscope, a phosphorescence spectroscope, a luminescence spectroscope, a spectrophotometer, a photometer, and the like. Various synthetic components are also utilized, or adapted for, use in the systems of the invention including, e.g., automated nucleic acid synthesizers, e.g., for synthesizing the oligonucleotides described herein. Detectors and synthetic components that are optionally included in the systems of the invention are described further in, e.g., Skoog et al., *Principles of Instrumental Analysis*, $5^{th}$ Ed., Harcourt Brace College Publishers (1998) and Currell, *Analytical Instrumentation: Performance Characteristics and Quality*, John Wiley & Sons, Inc. (2000), both of which are incorporated by reference.

The systems of the invention also typically include controllers that are operably connected to one or more components (e.g., detectors, synthetic components, thermal modulator, fluid transfer components, etc.) of the system to control operation of the components. More specifically, controllers are generally included either as separate or integral system components that are utilized, e.g., to receive data from detectors, to effect and/or regulate temperature in the containers, to effect and/or regulate fluid flow to or from selected containers, or the like. Controllers and/or other system components is/are optionally coupled to an appropriately programmed processor, computer, digital device, or other information appliance (e.g., including an analog to digital or digital to analog converter as needed), which functions to instruct the operation of these instruments in accordance with preprogrammed or user input instructions, receive data and information from these instruments, and interpret, manipulate and report this information to the user. Suitable controllers are generally known in the art and are available from various commercial sources.

Any controller or computer optionally includes a monitor which is often a cathode ray tube ("CRT") display, a flat panel display (e.g., active matrix liquid crystal display, liquid crystal display, etc.), or others. Computer circuitry is often placed in a box, which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user. These components are illustrated further below.

The computer typically includes appropriate software for receiving user instructions, either in the form of user input into a set of parameter fields, e.g., in a GUI, or in the form of preprogrammed instructions, e.g., preprogrammed for a variety of different specific operations. The software then converts these instructions to appropriate language for instructing the operation of one or more controllers to carry out the desired operation. The computer then receives the data from, e.g., sensors/detectors included within the system, and interprets the data, either provides it in a user understood format, or uses that data to initiate further controller instructions, in accordance with the programming, e.g., such as controlling fluid flow regulators in response to fluid weight data received from weight scales or the like.

The computer can be, e.g., a PC (Intel x86 or Pentium chip-compatible DOS™, OS2™, WINDOWS™, WINDOWS NT™, WINDOWS95™, WINDOWS98™, WINDOWS2000™, WINDOWS XP™, LINUX-based machine, a MACINTOSH™, Power PC, or a UNIX-based (e.g., SUN™ work station) machine) or other common commercially available computer which is known to one of skill. Standard desktop applications such as word processing software (e.g., Microsoft Word™ or Corel WordPerfect™) and database software (e.g., spreadsheet software such as Microsoft Excel™, Corel Quattro Pro™, or database programs such as Microsoft Access™ or Paradox™) can be adapted to the present invention. Software for performing, e.g., controlling temperature modulators and fluid flow regulators is optionally constructed by one of skill using a standard programming language such as Visual basic, Fortran, Basic, Java, or the like.

Figure 2:
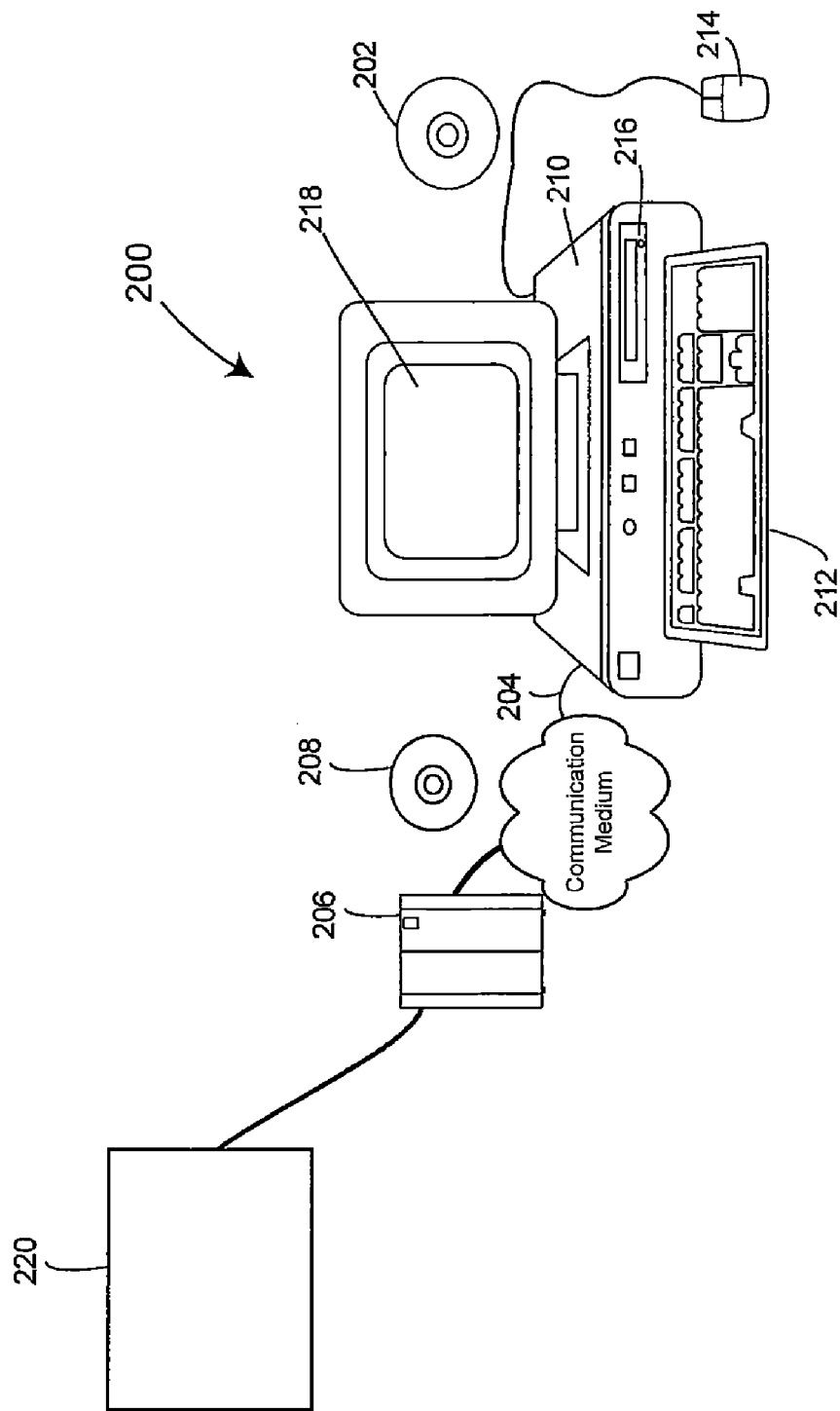
FIG. 2 is a block diagram showing a representative example system including a computer and a computer readable medium in which various aspects of the present invention may be embodied.

FIGS. 1 and 2 are schematics showing representative example systems that include logic devices in which various aspects of the present invention may be embodied. As will be understood by practitioners in the art from the teachings provided herein, the invention is optionally implemented in hardware and/or software. In some embodiments, different aspects of the invention are implemented in either client-side logic or server-side logic. As will be understood in the art, the invention or components thereof may be embodied in a media program component (e.g., a fixed media component) containing logic instructions and/or data that, when loaded into an appropriately configured computing device, cause that device to perform according to the invention. As will also be understood in the art, a fixed media containing logic instructions may be delivered to a viewer on a fixed media for physically loading into a viewer's computer or a fixed media containing logic instructions may reside on a remote server that a viewer accesses through a communication medium in order to download a program component.

In particular, FIG. 1 schematically illustrate computer 100 to which detector 102 and fluid transfer component 104 are operably connected. Optionally, detector 102 and/or fluid transfer component 104 is operably connected to computer 100 via a server (not shown in FIG. 1). During operation, fluid transfer component 104 typically transfers fluids, such as sample aliquots comprising labeled HPV amplicons to oligonucleotide array 106. Thereafter, detector 102 typically detects detectable signals (e.g., fluorescent emissions, etc.) produced by labeled amplicons that hybridize with oligonucleotides attached to oligonucleotide array 106 after one or more washing steps are performed to wash away non-hybridized nucleic acids from oligonucleotide array 106 using fluid transfer component 104. As additionally shown, thermal modulator 108 is also operably connected to computer 100. Prior to performing a hybridization assay, target HPV nucleic acids can be amplified using labeled primer nucleic acids. The amplicons of these amplification reactions are then typically transferred to oligonucleotide array 106 using fluid transfer component 104, as described above, to perform the binding assay. In some embodiments, binding assays are performed concurrently with HPV nucleic acid amplification in thermal modulator 108 using, e.g., molecular beacons, 5'-nuclease probes, or the like that comprise sequences selected from, e.g., SEQ ID NOS: 1-31. In these embodiments, detector 102 detects detectable signals produced as the amplification reactions are performed using thermal modulator 108.

FIG. 2 schematically shows information appliance or digital device 200 that may be understood as a logical apparatus that can read instructions from media 202 and/or network port 204, which can optionally be connected to server 206' having fixed media 208. Digital device 200 can thereafter use those instructions to direct server or client logic, as understood in the art, to embody aspects of the invention. One type of logical apparatus that may embody the invention is a computer system as illustrated in 200, containing CPU 210, optional input devices 212 and 214, disk drives 216 and optional monitor 218. Fixed media 202, or fixed media 208 over port 204, may be used to program such a system and may represent a disk-type optical or magnetic media, magnetic tape, solid state dynamic or static memory, or the like. In specific embodiments, the invention may be embodied in whole or in part as software recorded on this fixed media. Communication port 204 may also be used to initially receive instructions that are used to program such a system and may represent any type of communication connection. Optionally, the invention is embodied in whole or in part within the circuitry of an application specific integrated circuit (ACIS) or a programmable logic device (PLD). In such a case, the invention may be embodied in a computer understandable descriptor language, which may be used to create an ASIC, or PLD.

FIG. 2 also includes automatic synthesizer 220, which is operably connected to digital device 200 via server 206. Optionally, automatic synthesizer 220 is directly connected to digital device 200. During operation, automatic synthesizer 220 typically receives instructions to synthesize one or more oligonucleotides that comprise a sequence selected from, e.g., SEQ ID NOS: 1-31 or complements thereto, which are included in a data set comprised by, e.g., digital device 200 and/or a computer readable medium, such as fixed media 202 and/or 208.

XI. Kits

The oligonucleotides employed in the methods of the present invention are optionally packaged into kits. In addition, the kits may also include suitably packaged reagents and materials needed for DNA immobilization, hybridization, and detection, such solid supports, buffers, enzymes, and DNA standards, as well as instructions for conducting the assay. Optionally, the oligonucleotides of the invention are provided already attached or otherwise immobilized on solid supports. As another option, oligonucleotides are provided free in solution in containers, e.g., for performing the detection methods of the invention in the solution phase. In some of these embodiments, oligonucleotides of the kits comprise labels and/or quencher moieties, such as when molecular beacons, 5'-nuclease probes, or the like comprise sequences selected from, e.g., SEQ ID NOS: 1-31. In certain embodiments, kits further include labeled primers for amplifying target HPV sequences in a sample.

The kits also typically include one or more of: a set of instructions for contacting the oligonucleotides with nucleic acids from a sample or amplicons thereof and detecting binding between the oligonucleotides and HPV nucleic acids, if any, or at least one container for packaging the oligonucleotides and the set of instructions. Exemplary solid supports include in the kits of the invention are optionally selected from, e.g., a plate, a bead, a microwell plate, a microbead, a fiber, a whisker, a comb, a hybridization chip, a membrane, a single crystal, a ceramic layer, a self-assembling monolayer, or the like.

In some embodiments, the kit further includes at least one primer nucleic acid that is at least partially complementary to at least one segment of the L1 region of HPV, e.g., for amplifying a segment of that region of the HPV genome. In these embodiments, the kit typically further includes a set of instructions for amplifying one or more subsequences of the L1 region of HPV with the primer nucleic acids, at least one nucleotide incorporating biocatalyst, and one or more nucleotides. In certain embodiments, the primer nucleic acids comprise at least one label (e.g., a fluorescent dye, a radioisotope, etc.). Suitable labels are described further herein. For example, the primer nucleic acid is optionally conjugated with biotin or a biotin derivative. In these embodiments, the kit typically further includes an enzyme conjugated with avidin or an avidin derivative, or streptavidin or a streptavidin derivative, e.g., for effecting the detection of binding between the oligonucleotides of the invention and target nucleic acids. In these embodiments, the kit generally further includes at least one nucleotide incorporating biocatalyst (e.g., a polymerase, a ligase, or the like). In these embodiments, the kit typically also further comprising one or more nucleotides, e.g., for use in amplifying the target nucleic acids. Optionally, at least one of the nucleotides comprises a label. In some of these embodiments, the kits further include at least one pyrophosphatase (e.g., a thermostable pyrophosphatase), e.g., for use in minimizing pyrophosphorolysis, uracil N-glycosylase (UNG), e.g., for use in applications where protection against carry-over contamination is desirable.

XII. Examples

Performance Data for Cross-Reactive Oligonucleotides

It is understood that the examples and embodiments described herein are for illustrative purposes only and are not intended to limit the scope of the claimed invention. It is also understood that various modifications or changes in light the examples and embodiments described herein will be suggested to persons skilled in the art and are to be included within the spirit and purview of this application and scope of the appended claims.

These examples show certain performance data for various HPV oligonucleotides of the present invention, which were utilized as probes in this example. More specifically, probe binding specificity for different high-and low-risk HPV targets as well as probe melting characteristics are illustrated in these examples.

Example 1

Probe Binding Specificity

Certain oligonucleotides were used as probes to test for the probe binding specificity of each oligonucleotide against or relative to various high-and low-risk HPV targets.

A. Materials & Methods

The specific oligonucleotides utilized as probes in these assays were A3X5XA (SEQ ID NO: 12), A3X5XC (SEQ ID NO: 15), and A3X5XD (SEQ ID NO: 16). A3X5XA is an unmodified oligonucleotide, while A3X5XC contains five modified nucleotide substitutions, namely, four 5-propynyl-dU substitutions and one 5-methyl-dC substitution. The A3X5XD oligonucleotide also includes five modified nucleotide substitutions at the same nucleotide positions as the A3X5XC oligonucleotide, but these modified nucleotides have different chemistries (i.e., four 2'-O-methyl Ribo-U substitutions and one 2'-O-methyl Ribo-C substitution).

Using a Sodium Phosphate/EDTA coat buffer solution mixed with approximately 100 picomoles of each desired probe per ml, microwell plates (MWP) were coated by pipetting 100 µl of probe solution into each well (resulting in a concentration of 10 pmoles/well), sealing with plastic, and incubating overnight at room temperature. Each plate was then washed with a buffer solution of PBS+EDTA, dried on the lab bench, bagged in plastic with dessicant, and stored at 4C.

Next, HPV plasmids were amplified in a PCR master mix including 10 mM Tris/50 mM KCl at pH8.3, 7.5 Units per reaction AmpliTaq Gold, 200 µM each of dATP, dCTP, dGTP, 400 uM dUTP, 0.5 µM each of upstream and downstream primers, 1 unit of UNG per reaction, 0.05% Sodium azide, 3.75 mM Magnesium Chloride, & 0.025% Tween-20 in a 100 µL reaction volume. The copy input for the low-risk genotypes indicated was $10^7$ copies per PCR, whereas that for the high-risk genotypes denoted was $10^4$ copies per PCR. The thermal cycling profile used on the PE 9700 was:

HOLD Program: 2 min 50° C.
HOLD Program: 9 min 95° C.
CYCLE Program (10 Cycles): 30 sec 95° C., 30 sec 48° C., 30 sec 72° C.
CYCLE Program (30 Cycles): 30 sec 95° C., 45 sec 54° C., 30 sec 72° C.
HOLD Program: 72° C. Indefinitely The ramp rate was set to 50%, the "Ramp Speed" was at "Max", and the "Reaction Volume" was "100 µL".

Following PCR amplification, the HPV amplicon was chemically denatured with 100 µL Denaturation Solution (1.6% (w/w) Sodium hydroxide, EDTA, Thymol blue) to form single-stranded DNA.

100 µL of HPV Hybridization Buffer (solution containing Sodium phosphate buffer, <25% Sodium thiocyanate and <0.2% solubilizer) was added to each well on the MWP. Then, 25 µL of denatured amplicon was added to the wells. The biotin-labeled HPV amplicon was hybridized to the oligonucleotide probes during incubation for 1 hour at 37° C. Following the hybridization, the MWP was washed with 1× Phosphate/Sodium chloride/EDTA buffer to remove unbound material. Avidin-Horseradish Peroxidase Conjugate was then added to each well of the MWP and incubated. The MWP was washed again to remove unbound conjugate and a substrate solution containing hydrogen peroxide and tetramethylbenzidine (TMB) was added to the wells.

The reaction was stopped by addition of a weak acid and the absorbance at 450 nm was measured using an automated microwell plate reader. These absorbance values were represented as bar graphs to show the relative OD readings obtained with the plate reader.

B. Results

Figure 3:
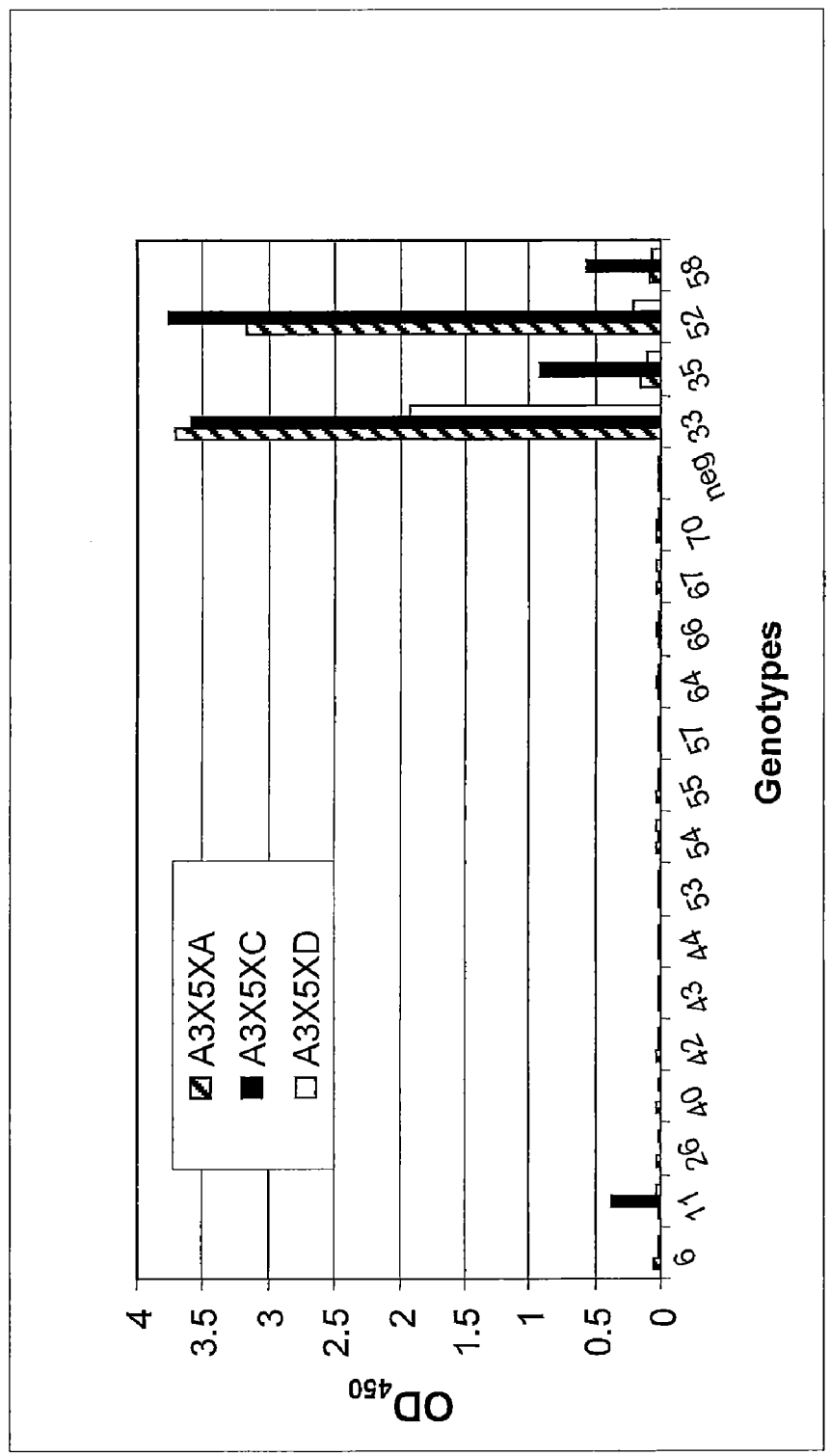
FIG. 3 is a graph showing the specificity of the A3X5X oligonucleotide series for various HPV targets.

FIG. 3 is a graph that illustrates the specificity of several probes for various HPV targets. In particular, the abscissa of the graph represents the absorbance for each polymerase chain reaction mixture amplicon, hybridized to the immobilized probe, subjected to an enzymatic color precipitation reaction and then measured at 450 nm, while the ordinate represents the genotypes of the particular HPV targets assayed. These specificity experiments have also been repeated using the A3X5XC oligonucleotide in a pool of several oligonucleotides specific to high risk HPV genotypes as well (data not shown).

Example 2

Probe Melting Characteristics

The unmodified A3X5XA oligonucleotide was compared with the modified A3X5XC oligonucleotide to examine the difference in melting temperature.

A. Materials & Methods

The oligonucleotides were each assayed at 0.1 micromolar (μM) in a buffer containing 120 mM potassium acetate pH 8.3, 50 mM tricine pH 8.3, 4.5% (w/v) glycerol, 200 μM each of dATP, dCTP, dGTP, 400 μM dUTP, 4 mM magnesium acetate pH 6.5, 0.4×SYBR® Green (from 10,000× stock), and 0.2 μM of complementary strand oligonucleotide.

The DNA strands in the buffer were first annealed by raising the temperature to 100 degrees C. and then lowering it to 35 degrees C. at 2 degrees/second. After annealing, the temperature was raised from 35 degrees C. to 70 degrees C. at 2 degrees/second to dissociate (melt) the DNA duplex. The change of state from double-strand to single-strand (DNA dissociation) as the temperature is raised results in a reduction of dye binding (SYBR® Green) to the DNA, and to a concomitant decrease in fluorescence. This change in fluorescent emission with temperature was measured in an ABI Prism® 7000 Sequence Detection System (Applied Biosystems, Foster City, Calif., USA) using the FAM filter (approximate maximum wavelength 515 nanometers). The derivatives of the resultant fluorescence readings were graphed versus temperature to more easily visualize the inflection point at which 50% of the duplex dissociated ($T_m$).

B. Results

Figure 4:
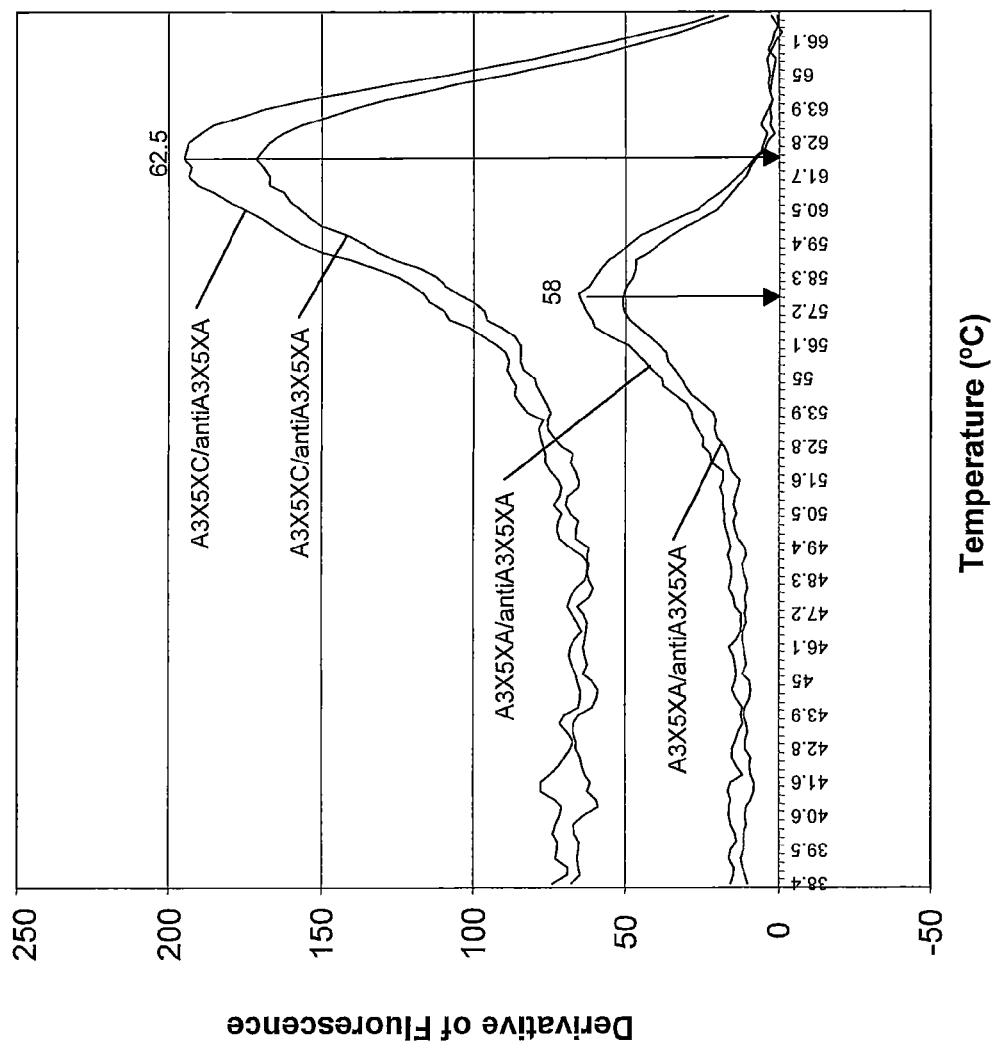
FIG. 4 is a melting curve for perfect match sequences.

FIG. 4 is a graph that shows melting curves for the A3X5XA and A3X5XC oligonucleotides using a complementary sequence with no mismatches (i.e., antiA3X5XA). The abscissa of the graph represents the derivative of the fluorescence, while the ordinate represents the temperature. As shown, a melting temperature increase of about 4.5° C. was detected for the A3X5XC oligonucleotide relative to the A3X5XA oligonucleotide using the perfect match complementary oligonucleotide.

Figure 5:
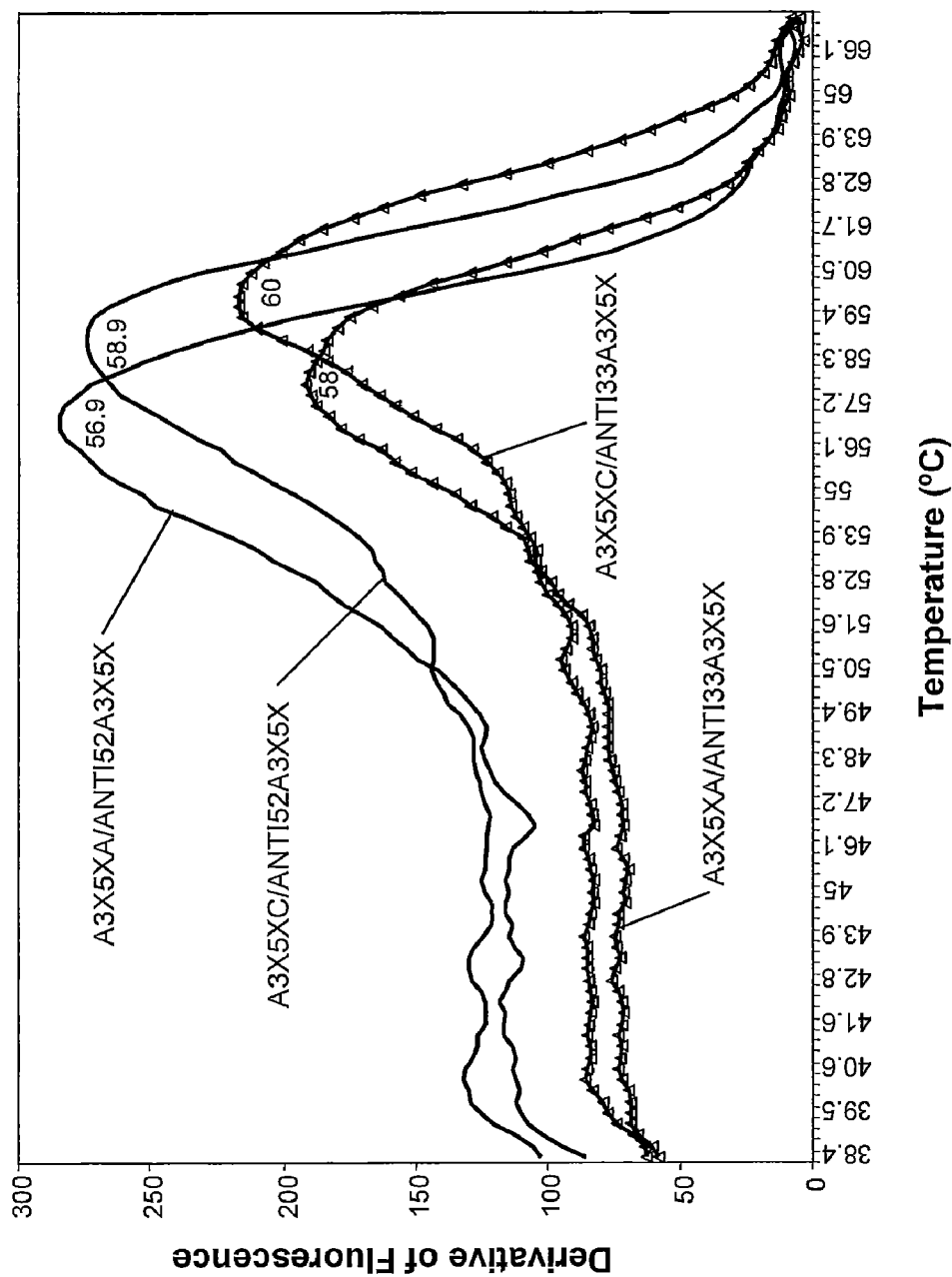
FIG. 5 is a melting curve for single mismatch sequences.

FIG. 5 is a graph that shows melting curves for the A3X5XA and A3X5XC oligonucleotides using two target sequences, anti33A3X5X and anti52A3X5X, that each included a single distinct mismatch to the oligonucleotides. The abscissa of the graph represents the derivative of the fluorescence, while the ordinate represents the temperature. As shown, the difference in melting temperature between the A3X5XA oligonucleotide and the A3X5XC oligonucleotide detected for target sequences was approximately 2.5° C.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. An oligonucleotide comprising a nucleic acid sequence having at least 95% sequence identity to one of SEQ ID NOS: 14, 17, 20, and 21 or a complement of one of SEQ ID NOS: 14, 17, 20, and 21, which oligonucleotide consists of 100 or fewer nucleotides.

2. The oligonucleotide of claim 1, further comprising at least one labeling moiety and/or at least one quencher moiety.

3. The oligonucleotide of claim 1, wherein the nucleic acid comprises at least one modified nucleotide substitution.

4. The oligonucleotide of claim 3, wherein the modified nucleotide is selected from the group consisting of: a C5-methyl-dC, a C5-ethyl-dC, a C5-methyl-dU, a C5-ethyl-dU, a 2,6-diaminopurine, a C5-propynyl-dC, a C5-propynyl-dU, a C7-propynyl-dA, a C7-propynyl-dG, a C5-propargylamino-dC, a C5-propargylamino-dU, a C7-propargylamino-dA, a C7-propargylamino-dG, a 7-deaza-2-deoxyxanthosine, a pyrazolopyrimidine analog, a pseudo-dU, a nitro pyrrole, a nitro indole, 2'-0-methyl Ribo-U, 2'-0-methyl Ribo-C, an 8-aza-dA, an 8-aza-dG, a 7-deaza-dA, a 7-deaza-dG, an N4-ethyl-dC, and an N6-methyl-dA.

5. A method of determining a presence of at least one high-risk human papillomavirus (HPV) type in a sample, the method comprising:
(a) contacting nucleic acids and/or amplicons thereof from the sample with at least one oligonucleotide that comprises a nucleic acid sequence having at least 95% sequence identity to one of SEQ ID NOS: 14, 17, 20, and 21 or a complement of one of SEQ ID NOS: 14, 17, 20, and 21, which oligonucleotide consists of 100 or fewer nucleotides; and,
(b) monitoring binding between the nucleic acids and/or amplicons thereof, and the oligonucleotide, wherein detectable binding between the nucleic acids and/or amplicons thereof, and the oligonucleotide, determines the presence of the high-risk HPV type in the sample.

6. The method of claim 5, wherein the high-risk HPV type comprises one or more of: HPV31, HPV33, HPV35, HPV52, HPV56, or HPV58.

* * * * *